(12) United States Patent
Reifenrath

(10) Patent No.: US 9,545,100 B2
(45) Date of Patent: Jan. 17, 2017

(54) PESTICIDAL COMPOSITIONS FOR INSECTS AND ARTHROPODS

(71) Applicant: Stratacor, Inc., Richmond, CA (US)

(72) Inventor: William Reifenrath, Novato, CA (US)

(73) Assignee: Stratacor, Inc., Richmond, CA (US)

( * ) Notice: Subject to any disclaimer, the term of this patent is extended or adjusted under 35 U.S.C. 154(b) by 80 days.

(21) Appl. No.: 14/268,726

(22) Filed: May 2, 2014

(65) Prior Publication Data
US 2015/0017217 A1 Jan. 15, 2015

Related U.S. Application Data

(63) Continuation of application No. 13/264,238, filed as application No. PCT/US2010/031408 on Apr. 16, 2010, now Pat. No. 8,911,757.

(60) Provisional application No. 61/170,259, filed on Apr. 17, 2009.

(51) Int. Cl.
| | | |
|---|---|---|
| A01N 37/02 | (2006.01) | |
| A01N 25/32 | (2006.01) | |
| A01N 37/00 | (2006.01) | |
| A61K 31/19 | (2006.01) | |
| A61K 31/20 | (2006.01) | |
| A01N 25/08 | (2006.01) | |

(52) U.S. Cl.
CPC .............. *A01N 25/08* (2013.01); *A01N 37/02* (2013.01)

(58) Field of Classification Search
None
See application file for complete search history.

(56) References Cited

U.S. PATENT DOCUMENTS

| | | | |
|---|---|---|---|
| 1,589,866 A | 6/1926 | Siegler | |
| 4,818,535 A | 4/1989 | Baines et al. | |
| 5,589,181 A | 12/1996 | Bencsits | |
| 5,693,344 A | 12/1997 | Knight et al. | |
| 5,711,953 A | 1/1998 | Bassett | |
| 6,147,091 A | 11/2000 | Kruger et al. | |
| 6,306,415 B1 * | 10/2001 | Reifenrath | A01N 63/02 424/401 |
| 6,444,216 B2 | 9/2002 | Reifenrath | |
| 6,869,613 B2 | 3/2005 | Kimler | |
| 6,953,814 B2 | 10/2005 | Reifenrath | |
| 8,142,801 B2 | 3/2012 | Jones | |
| 8,911,757 B2 * | 12/2014 | Reifenrath | A01N 37/02 424/405 |
| 2002/0054898 A1 | 5/2002 | Kimler | |
| 2006/0094601 A1 | 5/2006 | Hazen et al. | |

FOREIGN PATENT DOCUMENTS

| | | |
|---|---|---|
| CA | 873807 A | 6/1971 |
| FR | 2223049 A1 | 3/1973 |
| JP | 63246302 | 10/1988 |
| JP | 04342506 | 11/1992 |
| JP | 10067607 | 3/1998 |
| JP | 2000509402 | 7/2000 |
| JP | 2002249405 | 9/2002 |
| WO | 9502961 | 2/1995 |
| WO | 98/48623 A1 | 11/1998 |
| WO | 9900014 | 1/1999 |
| WO | 99/29171 A1 | 6/1999 |

OTHER PUBLICATIONS

U.S. Appl. No. 13/264,238, "Final Office Action", mailed Jan. 28, 2014, 8 pages.
U.S. Appl. No. 13/264,238, "Non-Final Office Action", mailed Jun. 13, 2013, 10 pages.
U.S. Appl. No. 13/264,238, "Notice of Allowance", mailed Nov. 7, 2014, 11 Pages.
U.S. Appl. No. 13/264,238, "Notice of Allowance", mailed Feb. 20, 2014, 5 pages.
U.S. Appl. No. 13/264,238, "Restriction requirement", mailed May 3, 2013, 5 pages.
Mullens et al., "Laboratory trials of fatty acids as repellents or antifeedants against houseflies, horn flies and stable flies (Diptera: Muscidae)", *Pest Management Science*, vol. 65, No. 12, 2009, pp. 1360-1366.
Siegler et al., "The fatty acids as contact insecticides", J. Econ. Entomol., 18:292-299 (1925).
Examination Report No. 2 issued on Jul. 9, 2014 in the Australian Patent Application No. 2010236258, 4 pages.
Notice of Reasons for Rejection issued on Jun. 10, 2014 in the Japanese Patent Application No. 2012-505962, with English translation, 8 pages.
Office Action issued on May 2, 2014 in the Mexican Patent Application No. MX/a/2011/010940, with partial translation, 5 pages.
Second Office Action issued on Nov. 12, 2014 in the Mexican Patent Application No. MX/a/2011/010940, with partial translation, 8 pages.
Australian Patent Application No. 2010236258, Examination Report No. 1 mailed Jan. 24, 2014, 4 pages.

(Continued)

*Primary Examiner* — Alton Pryor
(74) *Attorney, Agent, or Firm* — Kilpatrick Townsend & Stockton LLP

(57) ABSTRACT

The present invention provides an insect or arthropod pesticidal composition. The composition includes active ingredients having a mixture of fatty acids, each of the fatty acids having a straight carbon chain from 6 to 12 carbon atoms long. The fatty acid mixture includes a first fatty acid molecule having a straight carbon chain from 6 to 8 carbon atoms long, and a carboxylic acid group. The fatty acid mixture also includes a second fatty acid molecule having a straight carbon chain from 8 to 12 carbon atoms long, and a carboxylic acid group. The composition also includes a carrier that promotes adherence or absorption or transport across the surface of insects or arthropods to effect their incapacitation or death.

31 Claims, 18 Drawing Sheets

(5 of 18 Drawing Sheet(s) Filed in Color)

(56) References Cited

OTHER PUBLICATIONS

Chansang et al., "Field evaluation of repellents and insecticidal aerosol compositions for repelling and control of Siphunculina funicola (Diptera: Chloropidae) on aggregation sites in Thailand," J Am Mosq Control Assoc, Jun. 2008; 24(2): 299-307.

Columbian Patent Application No. 11-149.286, Office Action dated Jul. 25, 2013, 10 pages.

Columbian Patent Application No. 11-149.286, Office Action dated Feb. 21, 2014, 3 pages.

International Search Report and Written Opinion dated Jan. 3, 2011, issued in related International Patent Appln. No. PCT/US2010/031408, filed Apr. 16, 2010.

Notice of Reasons for Rejection mailed on Feb. 18, 2014 in corresponding Japanese Application No. 2012-505962, with English Translation, 7 pages.

Reifenrath W.G., "Enhanced skin absorption and fly toxicity and Permethrin in Emulsion Formulation," 2007, Bull. Environ. Contam. Toxicol, vol. 78, pp. 299-303.

Skelton, et al., "Fatty Methyl Esters as Solvent Alternatives for Emulsifiable Concentrate Formulations," *Pesticide Formulations and Application Systems, ASTM Special Technical Publication*, vol. 18, pp. 185-194. (Jan. 1, 1998).

Skelton, et al., "Pesticide Microemulsion Concentrate Formulations Utilizing Fatty Acid Methyl Esters as Solvent Alternatives," *Pesticide Formulations and Application Systems, ASTM Special Technical Publication*, vol. 13, pp. 114-120 (Jan. 1, 1993).

Supplementary European Search Report for European Application No. EP 10765267.9, dated May 29, 2013, 6 pages.

\* cited by examiner

Insect Incapacitation after 10 minute Exposure to C8910/Kaolin Water Dispersion (filter paper/petri dish)

- Aedes aegypti
- House Fly
- Stable Fly
- Horn Fly

FIG. 3

Insect Incapacitation after 25 minute Exposure to C8910/Kaolin Water Dispersion (filter paper/petri dish)

- Aedes aegypti
- House Fly
- Stable Fly
- Horn Fly

Aedes aegypti incapacitation and mortality after exposure to C8910 water dispersion, Permethrin water dispersion, DEET Aqueous Soln. and Distilled Water treated filter papers/petri dish. All actives at dose of 4.7 ug/cm2

FIG. 7

House fly incapacitation and mortality after exposure to 15%C8910/Kaolin water dispersion, 1%Permethrin/Kaolin water dispersion, and Kaolin water dispersion (control) treated filter papers.

Space Spray for House Fly control in a Peet Grady Chamber

PESTICIDAL COMPOSITIONS FOR INSECTS AND ARTHROPODS

CROSS-REFERENCES TO RELATED APPLICATIONS

This application is a continuation application of U.S. patent application Ser. No. 13/264,238, filed Feb. 3, 2012, which is the U.S. National Stage entry under §371 of International Application No. PCT/US2010/031408, filed Apr. 16, 2010, which claims benefit of priority to U.S. Provisional Application No. 61/170,259, filed Apr. 17, 2009, the contents of which are incorporated by reference in their entirety for all purposes.

BACKGROUND

Mosquito borne diseases include malaria, yellow fever, and dengue fever. Malaria occurs in over 100 countries and approximately 40% of the world's population is at risk. According to the CDC, more than 1 million deaths each year are caused by malaria, mostly small children in African areas south of the Sahara. Ticks can transmit encephalitis, Lyme disease and Typhus fever. Filariasis can be transmitted by blackflies, leishmaniasis by sandflies, sleeping sickness by Tsetse flies, and Chagas disease by assassin bugs. Lice can spread typhus fever and fleas are the well-known vector for plague. While the common house fly (*Musca domestica*) does not bite, it can transmit typhoid fever, cholera, dysentery, pinworms, hookworms, and certain tape worms. Stable flies (biting house flies) can also transmit filth-related disease. Reducing bites or reducing fly landings reduces the chances of getting these diseases, and insect repellents (e.g. DEET or N,N-diethyl-m-toluamide) are recommended for this purpose.

Insecticides (e.g. pyrethrum or permethrin) used as sprays or bed-net impregnants also reduce bites. DEET is effective in repelling mosquitoes, but it is a poor fly repellent. Its efficacy against mosquitoes is limited to a few hours duration by high evaporative loss from the skin surface (about 70% of applied dose) and also by significant absorption into the skin (approximately 20%). The usefulness of permethrin for insect control rests largely on its ability to cause incapacitation and death after insects make contact with treated surfaces or sprays; its low vapor pressure (about $10^{-8}$ mm Hg@20° C.) makes it relatively useless as a repellent. Permethrin's insecticidal properties are maximized in emulsion formulations; however, these formulations also maximize skin absorption (about 30%) and human skin contact should be avoided. Permethrin's efficacy has been reduced by insect resistance (Saaverdra-Rodriguez, K., C. Strode, A. F. Suarez, I. F. Salas, H. Ranson, J. Hemingway and W C. Black IV. Quantitative Trait Loci Mapping of Genome Regions Controlling permethrin resistance in the mosquito *Aedes aegypti*. *Genetics*, 180: 1137-1152, 2008).

Blood-sucking insects use a variety of physical and chemical cues to seek out a host. Their behavior can also be modified by emissions or pheromones from themselves or other species. A better understanding of the chemical-mediated behavior has lead to the development of alternate control measures, such as mating disruption.

A variety of factors and chemicals, including fatty acids, have been implicated or suggested as mosquito host attractants, and the literature contains many contradictory reports. Brown lists a number of factors involved in the attraction of mosquito to humans (in order of importance): moisture, convective heat, carbon dioxide, movement, contour or increase in black-white interfaces, and reflectivity (Brown A. W. A., H. P. Roessler, E. Y. Lipsitz and A. G. Carmichael. Factors in the attractiveness of bodies for mosquitoes. *The Canadian Entomologist* 96:102-103, 1964).

Since 1995, we have been investigating fatty acids as repellants or biopesticides against insects and arthropods of medical or economical importance and acknowledge past support from the USDA (Reifenrath, W G. Natural Fly Repellent for Livestock. SBIR Phase II Final report, CSREES Award No. 2003-33610-13044, Feb. 1, 2007), US Army (Reifenrath, W G. Development of an Insect Repellent Based on Human Skin Emanations. Final Report, DAMD17-96-C-6046, October, 1996), and DoD (Reifenrath, W G. New Repellent Combination against Flies and Mosquitoes. Final Report, USAMRMC Award No. W81XWH-04-1-0787, Final Report, December 2006). Our approach has been utilitarian; that is, to first focus on low-cost formulations that had a reasonable chance of regulatory approval and to demonstrate that these formulations were effective in laboratory (Mullens, B A, Reifenrath, W G, and Butler, S M. Laboratory repellency trials of fatty acids against house flies, horn flies, and stable flies (Diptera: Muscidae). Pest Management Science, 65: 1360-1366, 2009; Reifenrath, W G. Natural Insect and Arthropod Repellent. U.S. Pat. No. 6,306,415 B1, Oct. 23, 2001) and field studies for insect control (Chansang, U. and Mulla, M. S. Field Evaluation of repellents and insecticidal aerosol compositions for repelling and control of *Siphunculina funicola* (Diptera: Chloropidae) on aggregation sites in Thailand. J. Am. Mosq. Control Assn. 24: 299-307, 2008; Reifenrath, W G. Natural Fly Repellent for Livestock, Stratacor, Inc. http://www.reeis.usda.gov/web/crisprojectpages/ 200581.html). Stratacor has an application approved by the U.S. EPA for a formulation of three medium chain fatty acids (octanoic, nonanoic, decanoic acids, trademarked C8910) for fly and lice control on cattle, as well as an approval for use of the three fatty acids on food commodity animals (Anonymous. Application to Register C8910 Fly Repellent Oil, Stratacor, Inc., Richmond Calif., Jan. 18, 2008; Anonymous. Notice of Pesticide Registration, C8910 Fly Repellent Oil, EPA Reg. No. 84893-1, Biopesticides and Pollution Prevention Division, Office of Pesticide Programs, U.S. Environmental Protection Agency, Washington, D.C., Oct. 13, 2009; Anonymous. Notice of Filing of a Pesticide Petition for Residues of Pesticide Chemicals in or on Various Commodities. US Environmental Protection Agency, Federal Register, Vol. 73, No. 54, Wednesday, Mar. 19, 2008; Anonymous. Memorandum, Tolerance Exemption Petition for the Active Ingredients C8-C10 n-carboxylic acids (octanoic acid, nonanoic acid, and decanoic acid), Biochemical Pesticides Branch, Biopesticides and Pollution Prevention Division, US Environmental Protection Agency, Washington, D.C., Oct. 8, 2009). These fatty acids have been approved by the US FDA as food additives (flavors) in the U.S. since 1965 and are categorized as "Generally Recognized as Safe". C8910 can be formulated for direct use on the skin, and a topical formulation is being advanced for human use in Africa. However, user compliance with topical repellents, even in the U.S. military, is low (about 30%). Therefore, our long term goal is to advance safe and cost-effective C8910 formulations for both direct skin application and area treatments or space sprays to control the spread of malaria by the *Anopheles* mosquito, filth related disease by house and stable flies, and tick borne diseases. The fatty acids comprising C8910 are inexpensive commodity chemicals that come from palm kernel oil or coconut oil (as a byproduct of coconut production) and from cattle tallow. These compounds could eventually be produced in developing countries.

Fatty acids of chain length 8 (caprylic or octanoic) to 11 (undecanylic acid) were reported to be toxic to house fly larvae (Quraishi, M. S. and A. J. Thorsteinson. Toxicity of some straight chain saturated fatty acids to house fly larvae. *J. Econ. Entomol.* 58: 400-402, 1965). The fatty acids octanoic, nonanoic, and undecylenic were found to have ovicidal activity against eggs of *Aedes aegypti*; the author suggested that the fatty acids exerted a "smothering" effect or interference with respiration (Cline, R. E. Lethal effects of aqueous formulations containing fatty amines or acids against eggs and larvae of *Aedes aegypti. J. Econ. Entomol.* 65: 177-181, 1972). The straight chain fatty acids (C7 to C11, but not C12) were found to be toxic to *Aedes aegypti* instar IV larvae and pupae (Quraishi, M. S. and A. J. Thorsteinson. Effect of synthetic queen substance and some related chemicals on immature stages of *Aedes aegypti. J. Econ. Entomol.* 58: 185-187, 1965). Caproic (C6) through capric acid (C10) were found to have optimal larvicidal activity for housefly larvae, with declining activity for undecanoic acid (C11) and lauric acid (C12) (Levinson, Z. H. and K. R. Simon Ascher. Chemicals affecting the pre-imaginal stages of the housefly. *Rivista DI Parassitologia.* 15: 111-119, 1954).

We have shown that C8910 is an effective mosquito repellent for use on the skin, and can also repel ticks, biting flies and significantly reduce the number of fleas and lice on animals. As a vapor phase repellent against mosquitoes, a number of straight and branched chain fatty acids have activity in olfactometer tests with *Aedes aegypti* mosquitoes (FIG. 1), with C8, C9, and C10 sitting at or near the top of the repellency "dome". As frequently seen in homologous series of insect repellents (Skinner, W. A. and Johnson, H. L. The design of insect repellents. In: *Drug Design*, Vol. 10, E J Ariens, Ed., Academic Press, New York, pp. 277-305, 1980), activity at lower chain length is limited by lack of persistence due to high volatility. Activity at higher chain length is limited by lack of volatility, as mosquito repellents are required to have a minimum effective evaporation rate (Reifenrath, W. G. and Robinson, P. B. In Vitro Skin Evaporation and Penetration Characteristics of mosquito repellents. *J. Pharm. Sci,* 71:1014-1018, 1982; Reifenrath, W. G. and Spencer, T. S. Evaporation and penetration from skin. In: *Percutaneous Absorption Mechanisms Methodology Drug Delivery*, R L Bronaugh and H I Maibach, Eds., 1st Ed., Marcel Dekker, New York, pp. 305-325, 1985).

The fatty acids comprising C8910 can penetrate the skin after topical application and can also "back diffuse" or reach the skin surface after application to the visceral side of the excised skin (Reifenrath, W. G. Unpublished data, Stratacor, Inc., December, 2005-February, 2006). However, these compounds are not effective insect repellents after oral administration to cattle (Personal Communication, David Boxler, Dept. of Entomology, University of Nebraska West Central Research and Extension Center, North Platte, Neb., Jun. 27, 2006), as they are metabolized too quickly to be excreted via the skin (Van Den Driessche, M., K. Peeters, P. Marien, Y. Ghoos, H. Devlieger, and G. Veerman-Wauters. Gastric emptying in formula-fed and breast-fed infants measured with the 13C-octanoic acid breath test. *J. Pediatr. Gastroenterol. Nutr.* 29: 46-51, 1999).

While conducting field studies on livestock, we were surprised to find that dusting cattle with C8910 offered protection (about 90% reduction in total body fly counts) against biting (horn) flies equal to the organophosphorus insecticides coumaphos (Co-ral[R]) and tetrachlorvinphos (Rabon[R]) (FIG. 2). These results have been reproduced by different investigators at different locations where temperature and humidity are high. In this type of test, C8910 was formulated as a dust and cattle self-treated by walking under a dust bag en-route to water. If C8910 were acting just as a repellent, the flies would simply have moved from the treated area (back) to the untreated areas (belly and legs), resulting in no net reduction in fly count. A direct toxic effect of C8910 on the flies could account for the efficacy, but this was not obvious at the time of the test. This prompted a laboratory examination of the incapacitative and toxic effects of C8910 on *Aedes aegypti* mosquitoes, which showed that direct contact (aqueous suspension of C8910 wettable powder on treated filter paper in Petri dishes) caused incapacitation in 10 minutes at a dose of 4.7 ug/cm$^2$, in 25 minutes at a dose of 2.35 ug/cm$^2$, and while a still lower dose of 1.18 ug/cm$^2$ did not cause incapacitation, it stopped spontaneous movement of mosquitoes, with negative consequences for mating and reproduction. Qualitatively similar activity was found in laboratory studies with house flies, stable flies, and horn flies (FIGS. 3-10), with house flies being least sensitive to the incapacitative and toxic effects of C8910. An initial report indicated that the Tsetse fly was not repelled by C8910 dust formulations (Personal Communication, Serap Aksoy, Dept. of Epidemiology and Public Health, Yale School of Medicine, New Haven, Conn., Apr. 21, 2003), but a later report showed that a 15% mineral oil and an 0.3% wettable powder dispersion were effective in incapacitating or killing the Tsetse fly (Personal Communication, Brian Weiss, Dept. of Epidemiology and Public Health, Yale School of Medicine, New Haven, Conn., Aug. 3, 2009). Tsetse fly repellency may have been compromised by incapacitation, an effect that was not appreciated until recently. In tests conducted in free choice cages as described by Mullens et al. (Mullens, B A, Reifenrath, W G, and Butler, S M. Laboratory repellency trials of fatty acids against house flies, horn flies, and stable flies (Diptera: Muscidae). *Pest Management Science,* 65: 1360-1366, 2009), the German cockroach became incapacitated and then died after roaming into floor areas treated with 15% C8910 in attapulgite clay (FIG. 11).

We have found that incapacitative and toxic effects of fatty acids on mosquitoes are highly dependent on the type of fatty acid and the formulation. When moisture is introduced in the form of aqueous dispersions of powder formulations, house fly and mosquito incapacitation and death result. Likewise, with mineral oil formulations. Both of these formulations enhance the mammalian skin absorption of C8910 and likely enhance fly uptake and absorption. Formulations made from emulsifiable concentrates (EC) promote skin absorption and enhance fly toxicity of permethrin (Reifenrath, W G. Enhanced skin absorption and fly toxicity of permethrin in emulsion formulation. *Bull. Environ. Contam. Toxicol.* 78: 299-303, 2007). Likewise, formulations of C8910 in EC cause house fly and mosquito toxicity. The well-known insecticidal properties of soaps (sodium or potassium salts of fatty acids), where the fatty acid is ionized at basic pH, is probably due to a different mechanism related to surfactant effects. Indeed, the ionic and non-ionic surfactants contained in an emulsifiable concentrate vehicle for permethrin (Evercide emulsifiable concentrate without permethrin, MGK Corp, Minneapolis) had no fly incapacitative effects. Incapacitation was not simply due to acidic pH, as lactic acid, a low molecular weight carboxylic acid, was nontoxic to flies in these assays. Lauric acid, with increased carboxylic acid carbon chain length beyond those comprising C8910, was also non-toxic in EC formulation. The insect repellent DEET did cause fly and mosquito mortality after 24 hours at 47 ug/cm$^2$ (the fatty acid dose that caused 100% immediate fly and mosquito incapacitation and 80-100% mortality at 24 hours), but by a mechanism that did not involve immediate incapacitation. As a test of a sodium ion channel blocker, freshly prepared aqueous emulsions of lidocaine free base (47 ug/cm$^2$) or 15% concentration in mineral oil did not cause fly incapacitation in these assays. At a dose of 4.7 ug/cm$^2$, permethrin caused irreversible fly and mosquito incapacitation, while the same low dose of C8910 showed reversible incapacitation against the stable fly and horn fly (FIGS. 9,10).

Observationally, the fatty acids comprising C8910 appear to have a selective repellent and/or toxic effect against mosquitoes and a variety of other flies, as spiders, bumble bees, honey bees, and wasps are unaffected. Ticks (*Ixodes pacificus* or *Dermacentor*) placed in the barren center of free choice cages and allowed to roam into quadrants of C8910 laden granules or carrier-only treated quadrants typically get within ½ inch of the repellent granules, do an about-face, and proceed into and through control areas and climb the walls of the cage, when they were captured by the investigator and placed back into the starting center. Occasionally, a tick will wander between repellent granules, and no longer having a choice between repellent and non-repellent areas, may continue to wander aimlessly in contact with the repellent, until it stopped all movement and eventually died. Forced exposure of ticks (*Ixodes pacificus*) to a 0.3% formulation of C8910 in Kaolin-P water dispersion for 10 minutes in a Petri dish resulted in 50% incapacitation, 100% incapacitation in 40 minutes and 100% mortality in 24 hours. No incapacitation or toxicity was observed with control (kaolin clay water dispersion) over 24 hours. A similar type of behavior was observed with the German cockroach, as noted above (FIG. 11). While these are descriptive accounts, they go to the heart of the proposed mechanism of fatty acid toxicity to susceptible insects—an indirect effect based on interference with the insect's ability to navigate, giving the appearance of death before actual death (the "living dead" or paralysis syndrome). At low levels comparable to natural pheromone concentrations, the fatty acids of C8910 may actually be attractive, and this has been observed with ants. Higher air concentrations of subject fatty acids may overload sensory mechanisms, and insects are repelled. If C8910 is forced into contact with susceptible insects in a spray formulation that promotes adherence to the insect or absorption by the insect (in effect surrounding the insect with C8910), reversible incapacitation may result at lower doses to the insect. At higher doses, the incapacitation becomes irreversible and the insect eventually dies.

BRIEF SUMMARY OF THE INVENTION

In one embodiment, the present invention provides an insect or arthropod pesticidal composition. The composition includes an active ingredient having a mixture of fatty acids, each fatty acid having a straight carbon chain from 6 to 12 carbon atoms long. The mixture of fatty acids includes a first fatty acid molecule having a straight carbon chain from 6 to 8 carbon atoms long, and a second fatty acid molecule having a straight carbon chain from 8 to 12 carbon atoms long. The pesticidal composition also includes a carrier that promotes absorption of the active ingredient by the insect or arthropod.

In a second embodiment, the present invention provides a method for incapacitating or killing an insect or arthropod, the method including contacting the insect or arthropod with the composition of the present invention.

BRIEF DESCRIPTION OF THE FIGURES

The patent or application file contains at least one drawing executed in color. Copies of this patent application publication with color drawing(s) will be provided by the Office upon request and payment of the necessary fee.

FIG. 3 shows insect incapacitation after 10 minute exposure to C8910/Kaolin water dispersion (filter paper/petri dish).

FIG. 4 shows insect incapacitation after 25 minute exposure to C8910/Kaolin water dispersion (filter paper/petri dish).

Figures 5, 6:
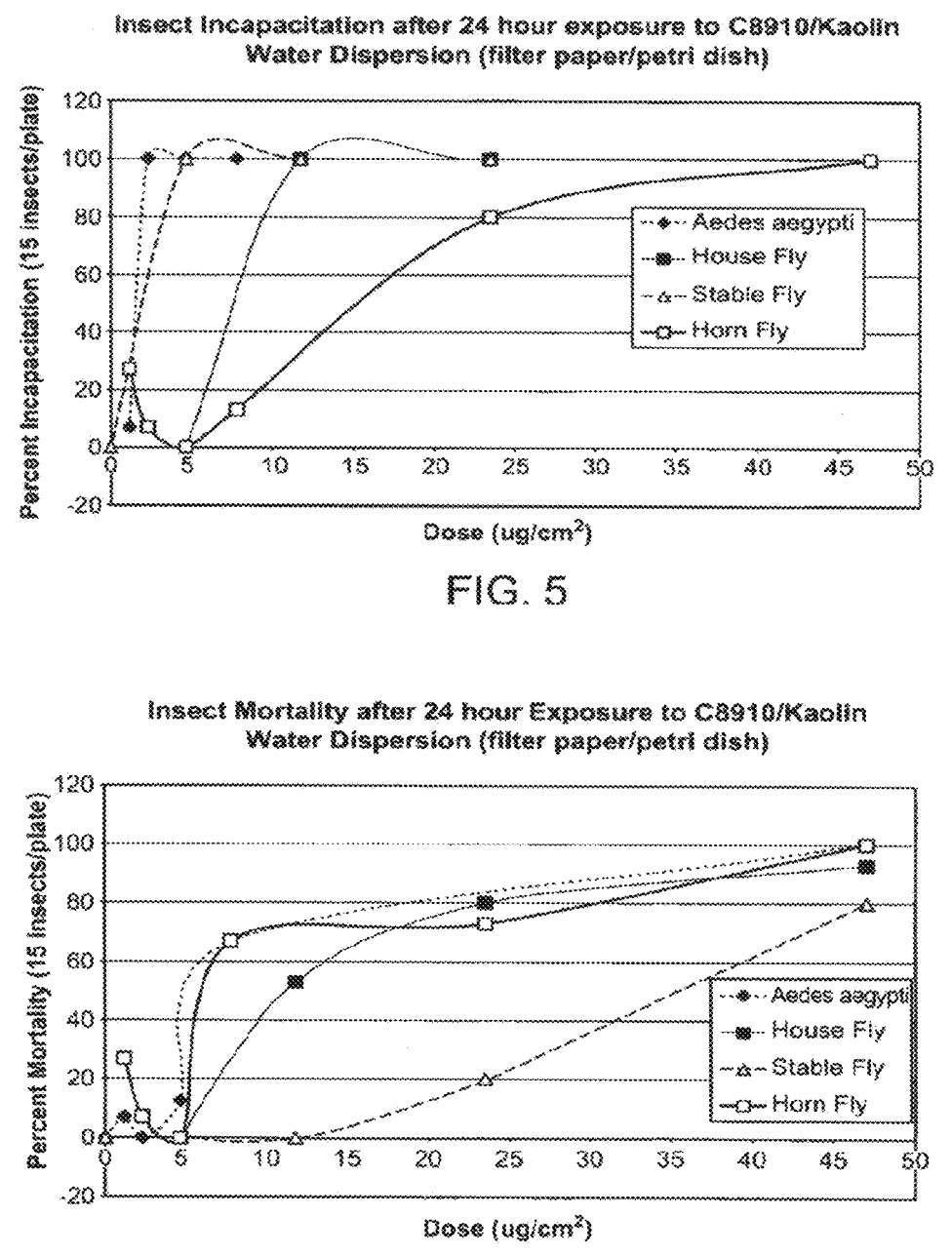

FIG. 5 shows insect incapacitation after 24 hour exposure to C8910/Kaolin water dispersion (filter paper/petri dish).

FIG. 6 shows insect mortality after 24 hour exposure to C8910/Kaolin water dispersion (filter paper/petri dish).

FIG. 7 shows *Aedes aegypti* incapacitation and mortality after exposure to C8910 water dispersion, Permethrin water dispersion, DEET aqueous solution, and distilled water treated filter papers/petri dish. All actives at dose of 4.7 μg/cm$^2$.

FIG. 8 shows house fly incapacitation and mortality after exposure to 15% C8910/Kaolin water dispersion, 1% Permethrin/Kaolin water dispersion, and Kaolin water dispersion (control) treated filter papers.

FIG. 14 shows house fly incapacitation vs. time after treatment with C8910 in dust formulation.

FIG. 15 shows house fly incapacitation from C8910 in emulsifiable concentrate (EC) vehicle, Run 1.

DETAILED DESCRIPTION OF THE INVENTION

I. General

Figure 1:
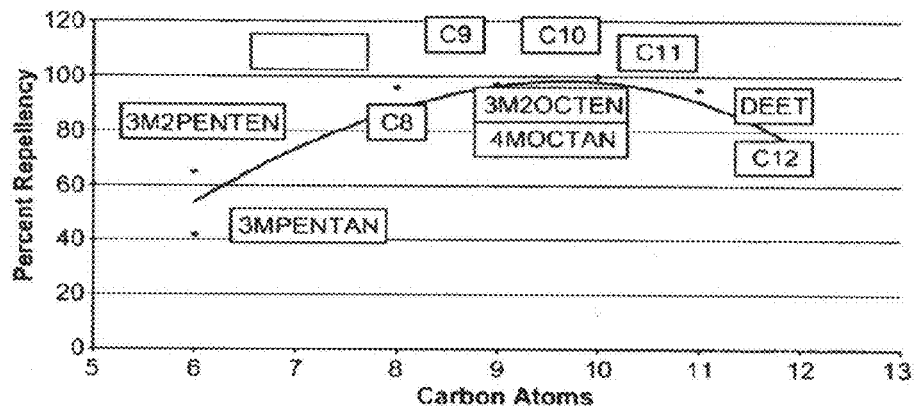
FIG. 1 shows repellency of fatty acids towards *Aedes aegypti* mosquitoes in an olfactometer. The straight chain fatty acids octanoic, nonanoic, decanoic, undecanoic, and lauric are designated as C8 through C12, respectively; 3-methylpentanoic acid as 3MPENTAN, 3-methyl-2-pentenoic acid as 3M2PENTEN, 2-octenoic acid as 2OCTEN, 3-methyl-2-octenoic acid as 3M2OCTEN, and 4-methyloctanoic acid as 4MOCTAN. N,N-Diethyl-m-toluamide is designated as DEET.
Figure 2:
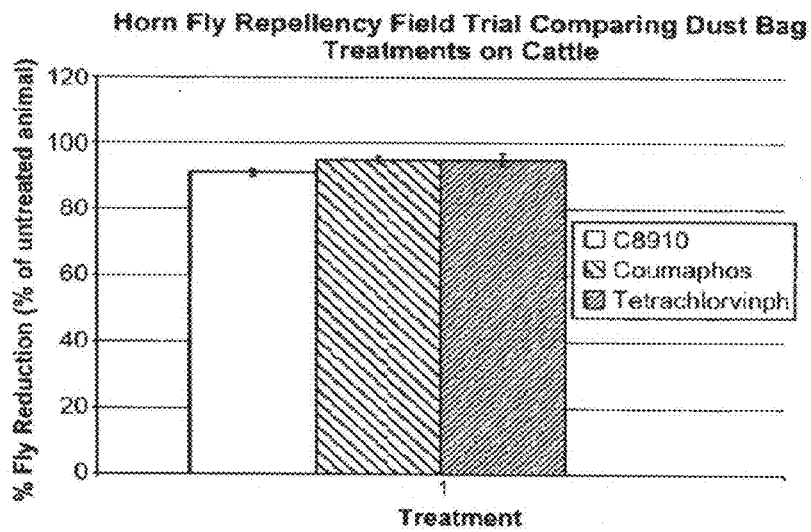
FIG. 2 shows horn fly repellency field trial comparing dust bag treatments on cattle.
Figure 9:
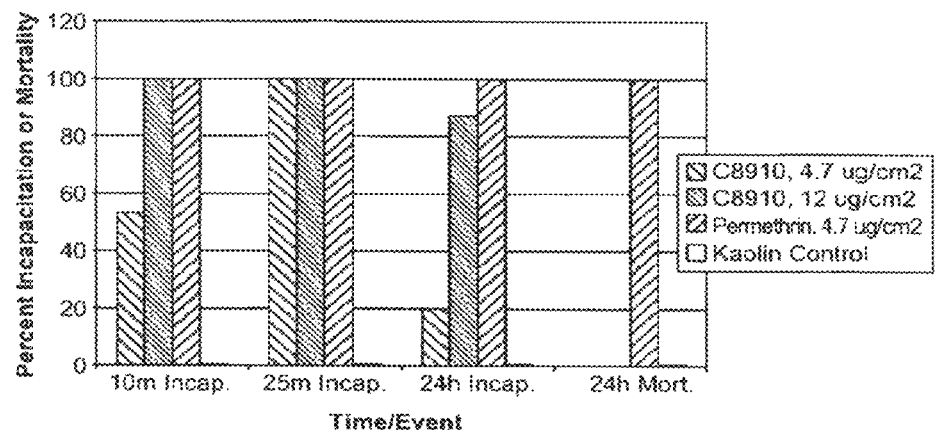
FIG. 9 shows stable fly incapacitation and mortality after exposure to 15% C8910/Kaolin water dispersion, 1% Permethrin/Kaolin water dispersion, and Kaolin water dispersion (control) treated filter papers.
Figure 10:
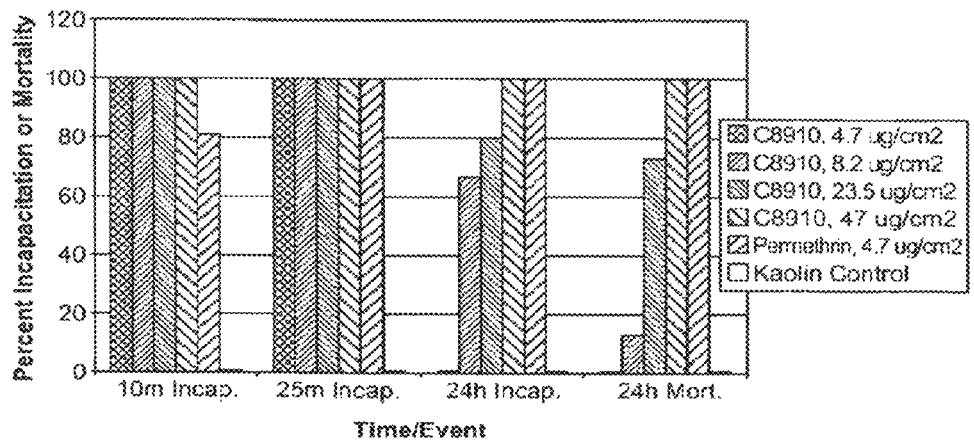
FIG. 10 shows horn fly incapacitation and mortality after exposure to 15% C8910/Kaolin water dispersion, 1% Permethrin/Kaolin water dispersion, and Kaolin water dispersion (control) treated filter papers.
Figure 11:
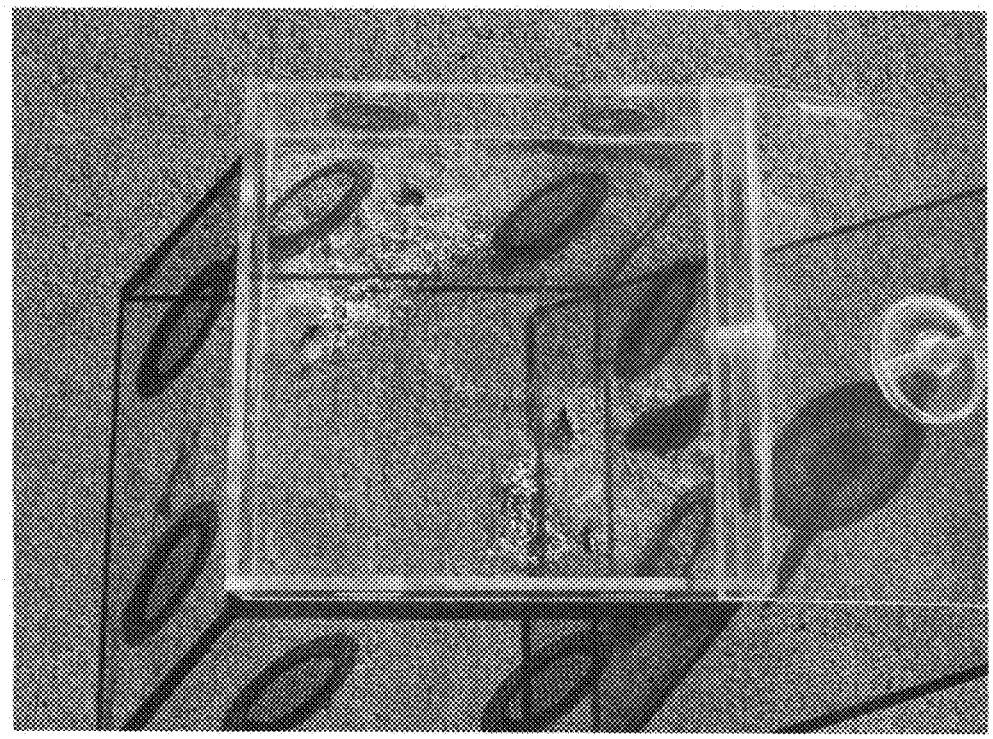
FIG. 11 shows free choice cage whose floor was divided into quadrants. Non-adjacent quadrants were treated with 15% C8910 in attapulgite clay, while remaining quadrants were untreated. German cockroaches introduced onto non treated surfaces became incapacitated and killed after entering C8910 treated quadrants.
Figure 12:
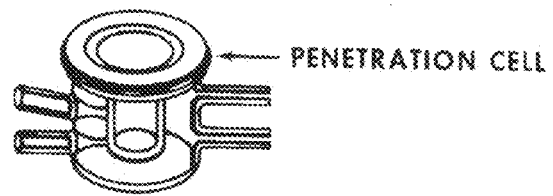
FIG. 12 shows penetration cell showing inner compartment for blood and water jacket for temperature control. A disc of skin is attached over the blood using a rubber O-ring.
Figure 13:
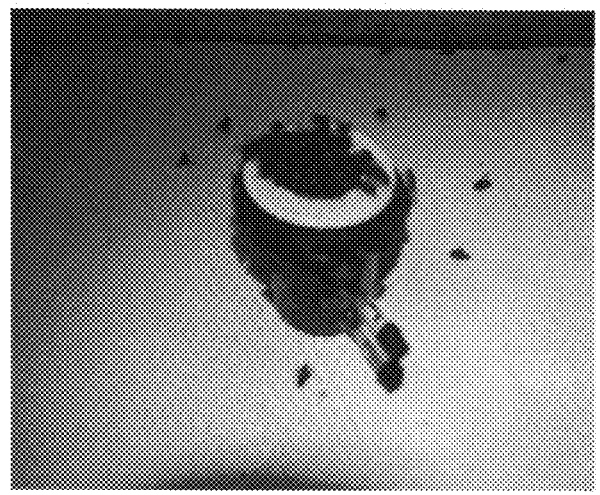
FIG. 13 shows stable flies attracted to blood-filled penetration cell fitted with skin.

The present invention provides compositions of octanoic acid, nonanoic acid and decanoic acid in combination with a carrier that promotes adherence or absorption or transport across the surface of insects or arthropods. The carrier can be Kaolin-P, a hydrated aluminum silicate, or Evercide without permethrin. The fatty acids are intermediaries in the energy metabolism occurring in living cells. Furthermore, all of the subject fatty acids have been used as food additives for half a century in the US and Europe, are categorized as Generally Recognized as Safe (GRAS) by the US FDA, and have very low environmental toxicity. Thus, it is surprising that contact or absorption of these fatty acids by the insect or arthropod surprisingly exerts a toxic effect. The use of the carrier increases the toxic effect of these compounds on the insects and arthropods by promoting adherence, absorption and transport across the surface of the insect or arthropod.

II. Definitions

"Arthropod" refers to members of the arthropod phyllum, including, but not limited to, ticks, spiders, scorpions, horseshoe crabs, centipedes, millipedes and other insects. Insects include, but are not limited to, mosquitoes, house flies, stable flies, horn flies, horse flies, face flies, eye flies, and biting midges.

"Pesticide" refers to a compound or substance that repels, incapacitates or kills a pest, such as an insect or arthropod.

"Carrier" refers to carrier for the active ingredient that promotes adherence or absorption or transport across the surface of insects or arthropods. The carrier can be any suitable material, such as a powder or solvent. Examples of carriers useful in the present invention include, but are not limited to, a wettable powder, an emulsifiable concentrate and an organic solvent. Emulsifiable concentrates are solutions capable of forming an emulsion, such as Evercide without the permethrin (provided by MGK Corporation, Minneapolis, Minn.). The emulsifiable concentrate enhances absorption of the solution by the insect. Wettable powders are those that are capable of absorbing water, such as Kaolin-P, a hydrated aluminum silicate.

"Incapacitate" refers to rendering an insect or arthropod unable to move, fly or escape.

As used herein, the term "fatty acid" refers to a carboxylic acid having an aliphatic tail, typically from 4 to 30 carbon atoms long. Fatty acids can be saturated, mono-unsaturated or poly-unsaturated. Fatty acids useful in the present invention also include branched fatty acids such as iso-fatty acids. Examples of fatty acids useful in the present invention, include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). One of skill in the art will appreciate that other fatty acids are useful in the present invention.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "organic solvent" refers to water-miscible or -immiscible solvents capable of dissolving either or both of water-soluble and water-insoluble organic compounds. Exemplary organic solvents useful in the present invention include, but are not limited to, hexanes, pentanes, benzene, toluene, pyridine, ethyl acetate, diethyl ether, methanol, ethanol, isopropanol, acetone, methylene chloride and chloroform. One of skill in the art will appreciate that other organic solvents are useful in the present invention.

III. Pesticidal Compositions and Methods of Using

The present invention provides pesticidal compositions for incapacitating or killing insects and arthropods. In some embodiments, the present invention provides an insect or arthropod pesticidal composition. The composition includes an active ingredient having a mixture of fatty acids, each fatty acid having a straight carbon chain from 6 to 12 carbon atoms long. The mixture of fatty acids includes a first fatty acid molecule having a straight carbon chain from 6 to 8 carbon atoms long, and a second fatty acid molecule having a straight carbon chain from 8 to 12 carbon atoms long. The pesticidal composition also includes a carrier that promotes absorption of the active ingredient by the insect or arthropod.

The fatty acids useful in the present invention can include any suitable fatty acids. Examples of fatty acids useful in the present invention, include, but are not limited to, hexanoic acid (C6), heptanoic acid (C7), octanoic acid (C8), nonanoic acid (C9), decanoic acid (C10), undecanoic acid (C11) and dodecanoic acid (C12). The fatty acids of the active ingredient can be present in any suitable amount. For example, the active ingredient can be from 1 to 99% by weight of the composition, preferably from about 5 to about 95% by weight, preferably from 1 to 50% by weight, preferably from 5 to 25% by weight, preferably about 15% by weight. In some embodiments, the first fatty acid molecule, the second fatty acid molecule and the third fatty acid molecule each comprise from about 5% to about 95% of the active ingredient. The fatty acids of the composition can be present in any suitable ratio. In some embodiments, the first, second and third fatty acid molecules are present in about a 1:1:1 ratio by weight.

In other embodiments, the carrier includes an emulsifiable concentrate. Emulsifiable concentrates include any composition forming an emulsion. Examples of emulsifiable concentrates include, but are not limited to, Evercide without the permethrin.

In some other embodiments, the carrier includes a wettable powder. Wettable powders useful in the present invention include any suitable powder that can be wet. Suitable powders can be inorganic materials such as clays, aluminates, silicates, or mixtures thereof, as well as polymeric materials. In some embodiments, the wettable powder is mixture of an aluminate and a silicate. In some other embodiments, the wettable powder is Kaolin-P.

In still other embodiments, the carrier includes an organic solvent. Organic solvents include, but are not limited to, hexanes, pentanes, benzene, toluene, pyridine, ethyl acetate, diethyl ether, methanol, ethanol, isopropanol, acetone, methylene chloride and chloroform. Other organic solvents are useful in the present invention.

In some embodiments, the second fatty acid molecule comprises a straight carbon chain from 8 to 9 carbon atoms long, and wherein the active ingredient further comprises (iii) a third fatty acid molecule having a straight carbon chain from 9 to 12 carbon atoms long, wherein the first fatty acid molecule, the second fatty acid molecule and the third fatty acid molecule are all different. In other embodiments, the first fatty acid molecule comprises octanoic acid, the second fatty acid molecule comprises nonanoic acid, and the third fatty acid molecule comprises decanoic acid.

In other embodiments, the active ingredient includes octanoic acid, nonanoic acid and decanoic acid at a ratio of about 1:1:1 by weight, and the carrier includes a member selected from the group consisting of emulsifiable concentrate and a wettable powder.

In a second embodiment, the present invention provides a method for incapacitating or killing an insect or arthropod, the method including contacting the insect or arthropod with the composition of the present invention. Any insect or arthropod is suitable for the methods of the present invention. In some embodiments, the insects or arthropods can be mosquitoes, house flies, stable flies, horn flies, horse flies, face flies, eye flies, biting midges, or ticks.

Incapacitating and insecticidal formulations were obtained from mixtures of semi-volatile fatty acids and carriers which allow adherence to or absorption by the insect or arthropod. The fatty acids served as the active species to incapacitate or kill the insect, while the vehicles served as adherence or absorption promoters of the fatty acids to the surface of the insects or arthropods. Formulations of 15% (w/w) fatty acids in kaolin clay were dispersed into water at various concentrations ranging from 1 part in 50 to 1 part in 2000 and applied to filter papers (one ml of formulation per 64 cm$^2$ of filter paper) enclosed in Petri dishes. Fifteen female *Aedes aegypti* mosquitoes were placed in the dishes and their fate observed over a 48 hour period. Relative to control treatments (water only, kaolin and water only), mosquitoes were incapacitated at dilutions down to 1 part in 1000 (0.015% actives) and were killed at dilutions down to 1 part in 500. A formulation of 15% fatty acids in an emulsifiable concentrate was applied to felt surfaces of free-choice cages (two 4"×4" treated areas and two 4"×4" control areas) in the laboratory and was shown to incapacitate house flies (*musca domestica*). Field application of this formulation was found to reduce resting house fly counts to a level comparable to permethrin treatments for periods up to twelve days. The active ingredients of these formulations, octanoic, nonanoic, and decanoic acids, are registered as GRAS by the U.S. FDA and should provide a safer and equally effective treatment as compared to traditional treatments that rely on organophosphates or pyrethroids.

Previous patents (U.S. Pat. Nos. 6,306,415, 6,444,216 and 6,953,814) describe a mixture of octanoic, nonanoic, and decanoic acid (C8910) for use as a fly repellent. This mixture can repel a variety of insects/arthropods to include house flies, stable flies (biting house fly), horn flies, mosquitoes, lice, and ticks. In the case of biting insects, their normal behavior is to seek out a host, such as a bird or a mammal for a blood meal, and its generally agreed that host emanations (moisture, carbon dioxide and others) guide the insect to the host. Application of semi-volatile chemicals to the skin (e.g. N,N-diethyl-m-toluamide or DEET) can interfere with normal host-seeking behavior and this activity is generally termed repellency, although the insect is not driven away per se. C8910 functions like DEET in that it interferes with host seeking behavior of mosquitoes. However, C8910 is a much better fly repellent than DEET and can reduce the fly count on treated livestock to a level comparable to that obtainable with pesticide treatments (Reifenrath, W G. Natural Fly Repellent for Livestock. SBIR Phase II Final report, CSREES Award No. 2003-33610-13044. Feb. 1, 2007). Observations in free choice cages (ventilated cages containing treated and untreated resting sites on the cage floor) indicated that C8910 not only reduced the fly count on treated surfaces, but also drove away flies from the surrounding (untreated) walls and ceilings of treated areas. DEET does not cause this effect.

C8910 was prepared in the form of a dust or emulsifiable concentrate and was dispersed or sprayed over treatment areas. Formulations of C8910 alone, permethrin alone and a combination of C8910 and permethrin were studied. It was concluded that fly reduction with C8910 alone was comparable to that obtained with the pesticide permethrin alone and that there was no significant advantage in combining these actives (Reifenrath, W G. New Repellent Combinations Against Flies and Mosquitoes. US. Army Medical Research Acquisition Activity. U.S. Army Medical and Material Command. Final Report. Contract No. W81XWH-04-1-0787, Apr. 12, 2006.).

Figures 14, 15:
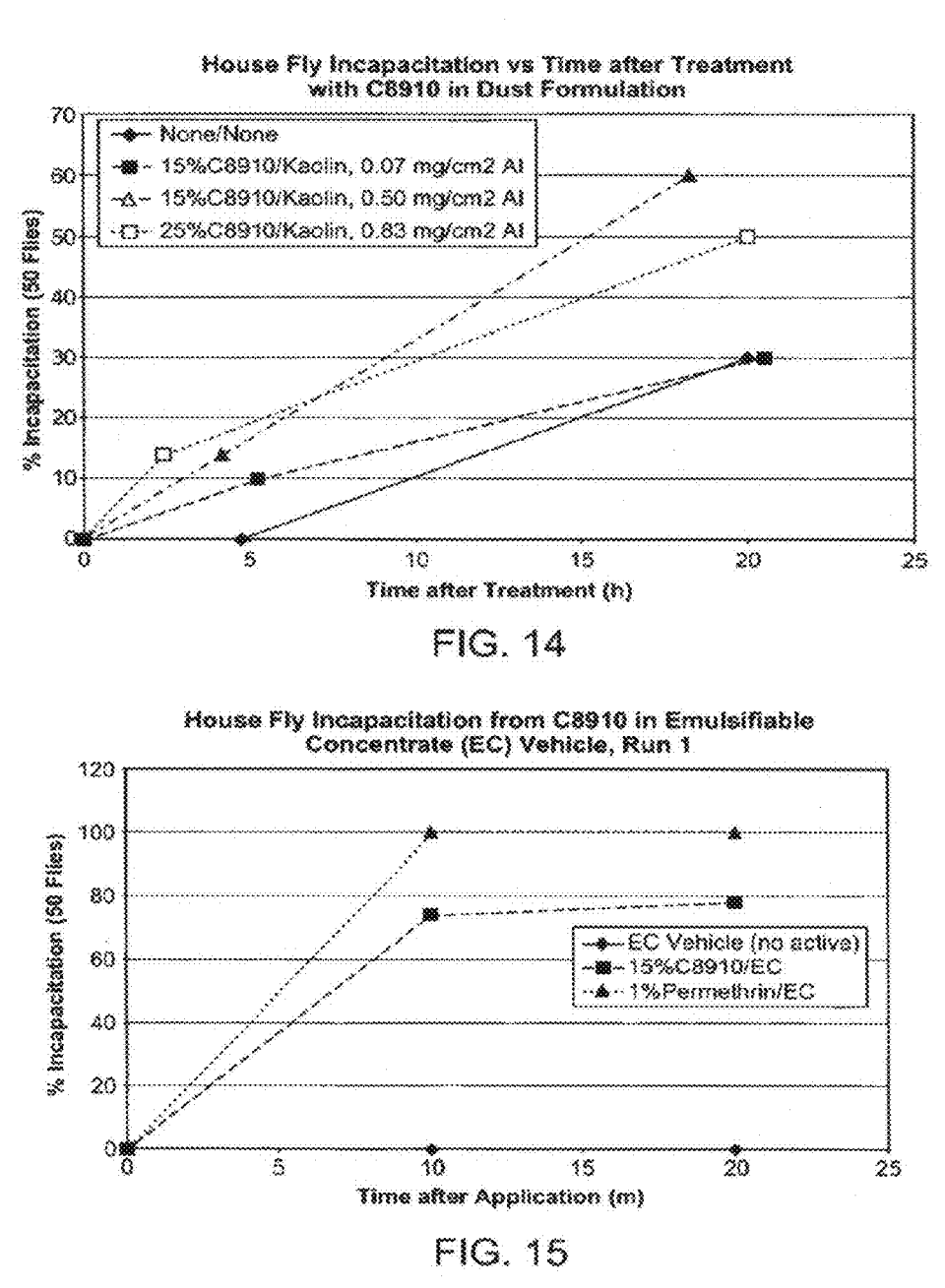
Figure 16:
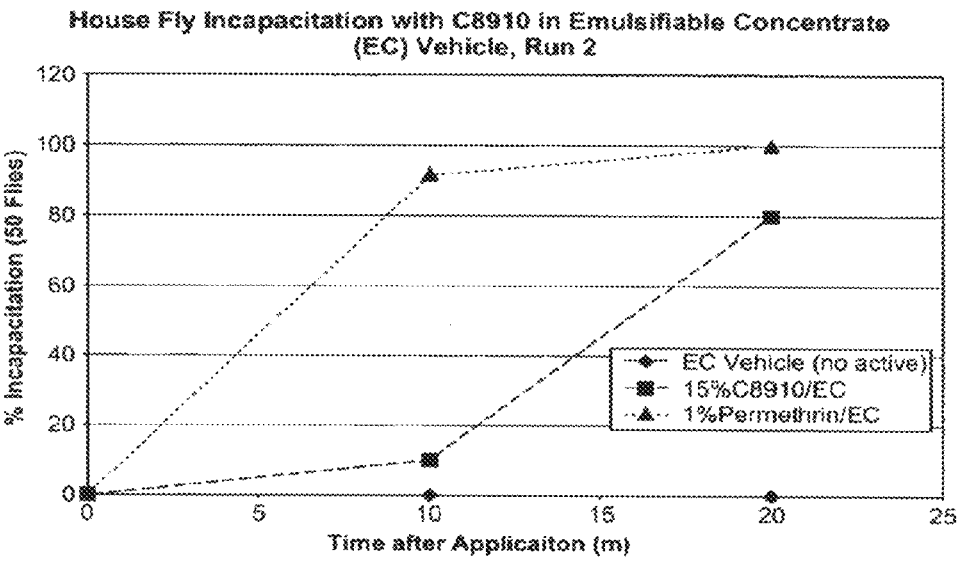
FIG. 16 shows house fly incapacitation from C8910 in emulsifiable concentrate (EC) vehicle, Run 2.

To examine the incapacitating effect of the C8910 composition further, we examined the effect of C8910 in dust formulation on house fly toxicity in the laboratory (free choice cages) and did observe an increase in fly incapacitation with an increase in the C8910 dose; the effect became more evident after approximately 20 hours of fly exposure (FIG. 14). However, when C8910 was formulated as an emulsion, fly toxicity increased dramatically (most flies incapacitated after 20 minutes, FIGS. 15 and 16), compared to no effect with the emulsion formulation control (no actives). After 2-3 hours, fly incapacitation for C8910 reached 94-100% in these trials. We have shown that emulsion formulation significantly increased fly toxicity and skin absorption of permethrin (Reifenrath, W G. Enhanced skin absorption and fly toxicity of permethrin in emulsion formulation. *Bull. Environ. Contam. Toxicol.* 2007, 78, 299-303), and emulsion formulation could enhance the bioavailability of C8910 to flies. C8910 equaled the outdoor house fly and eye fly control obtained with permethrin (FIGS. 17, 18 and 19), when both were formulated in an emulsifiable concentrate (Evercide, MGK Corp.) However, contact or absorption of these fatty acids by the fly would not be expected to exert a toxic effect, as these chemicals are intermediaries in the energy metabolism occurring in living cells. Furthermore, all of the subject fatty acids have been used as food additives for half a century in the US and Europe, are categorized as Generally Recognized as Safe (GRAS) by the US FDA, and have very low environmental toxicity. Fatty acids have been observed as emanations or surface chemicals of insects and these chemicals may play a role in their chemical signaling processes or defenses. Low level vapor exposure from C8910 may only result in repulsion from a host and no incapacitation. Higher level vapor exposure or physical contact with C8910 may result in a sensory overload, inhibiting the insect from performing those tasks consistent with life (e.g. an indirect toxic effect).

C8910 in dust formulation has reduced horn fly numbers on range cattle in several field trials in the southern United States (Texas and Kentucky). Control cattle had up to 1000 flies and C8910 reduced the total body number by approximately 90%. Treatment was applied using dust bags hung over gates leading to water holes. Thus, the animals self-treated by physical contact with the bag as it walked through the gate for water. The animals benefited from the repellent effect of C8910 in the treated skin areas, however, the flies could simply have moved to a non-treated area. To achieve the observed level of efficacy (total body reduction of flies), it was initially hypothesized that the animals dispersed the repellent over the body surface by rubbing against each other. However, it is now recognized that this high level of efficacy was the result of fly incapacitation and death from physical contact with C8910.

Figure 17:
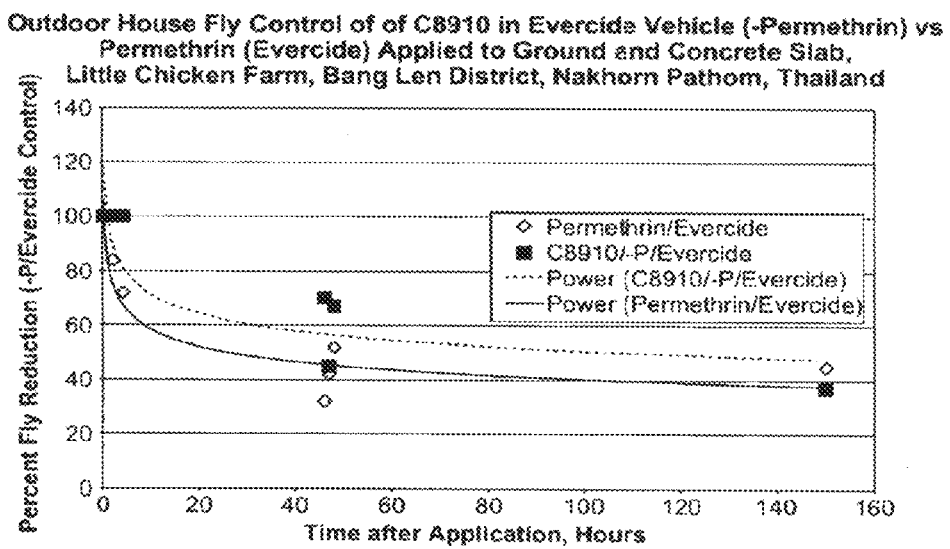
FIG. 17 shows outdoor house fly control of C8910 in Evercide vehicle (-Permethrin) vs. Permethrin (Evercide) applied to ground and concrete slab, Little Chicken Farm, Bang Len District, Nakhorn Pathom, Thailand.
Figure 18:
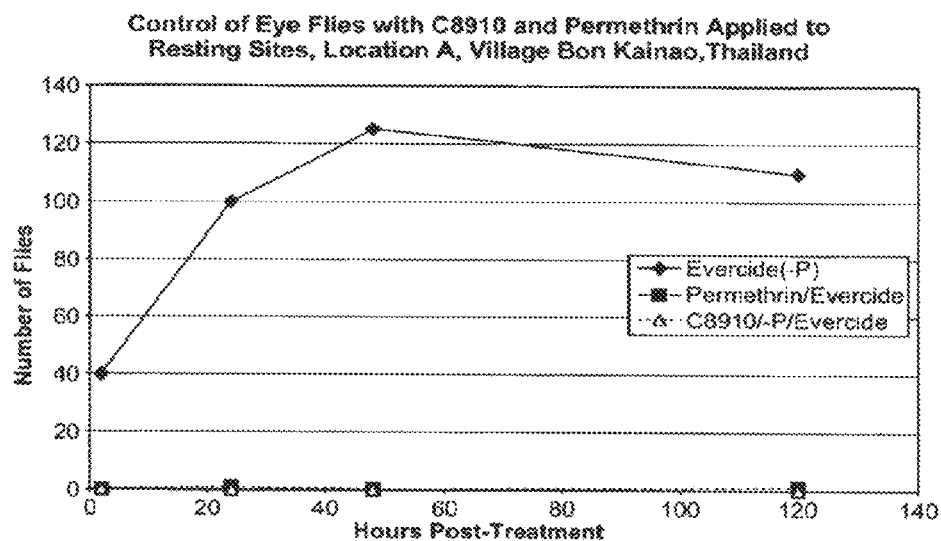
FIG. 18 shows control of eye flies with C8910 and Permethrin applied to resting sites, location A, Village Bon Kainao, Thailand.
Figure 19:
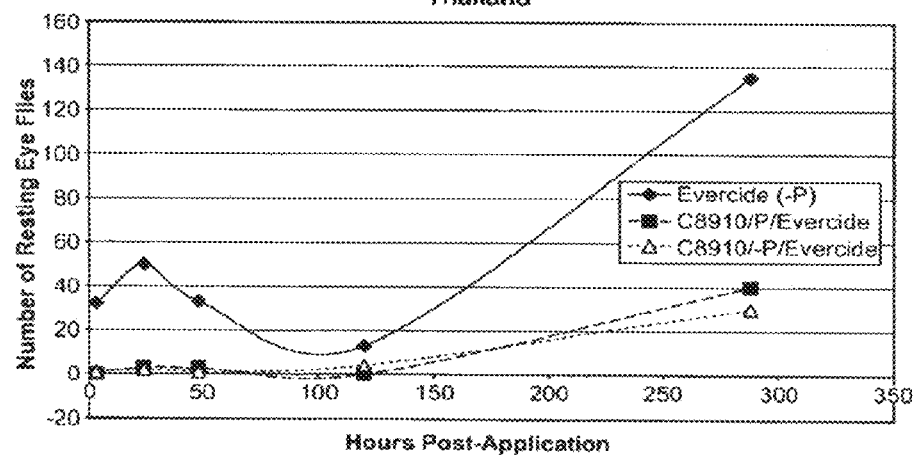
FIG. 19 shows control of eye fly with C8910 in Evercide, with and without Permethrin, applied to resting sites, Location B, Village Bon Kainao, Thailand.
Figure 20:
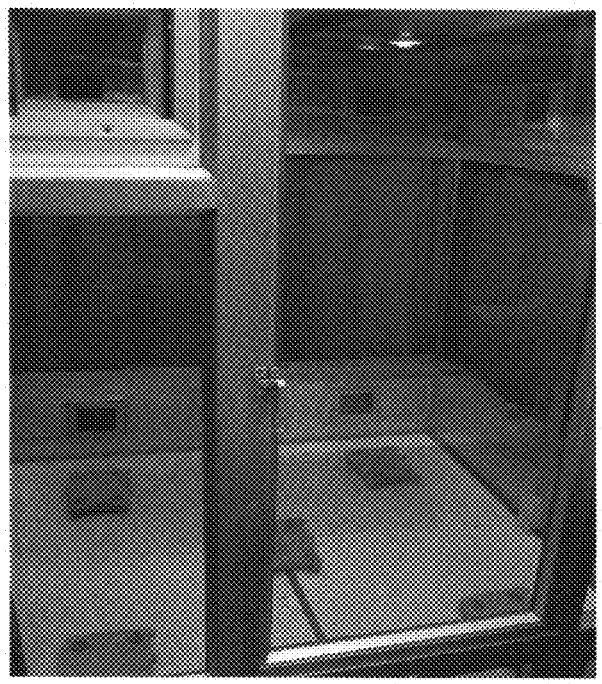
FIG. 20 shows the space spray for house fly control in a Peet Grady chamber.
Figure 21:
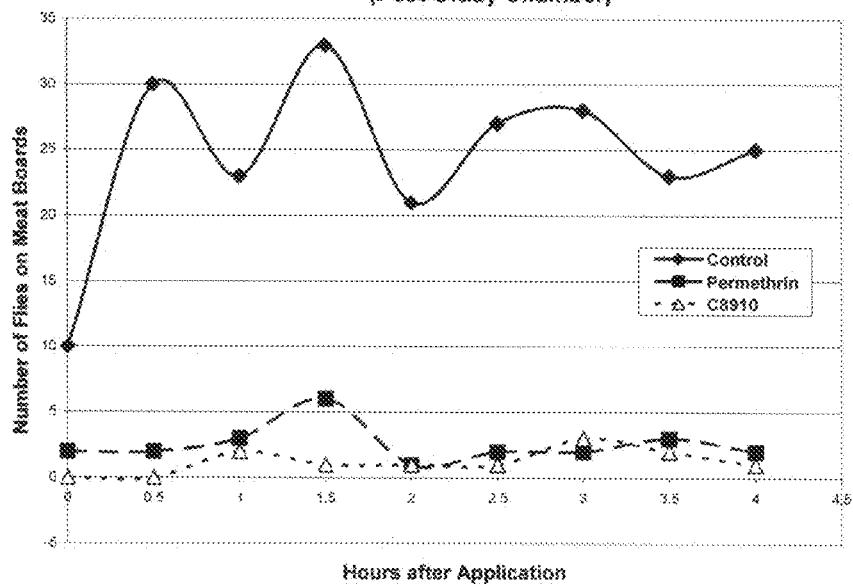
FIG. 21 shows house fly control of C8910 vs. Permethrin in Minugel 200 (Peet Grady chamber).
Figure 22:
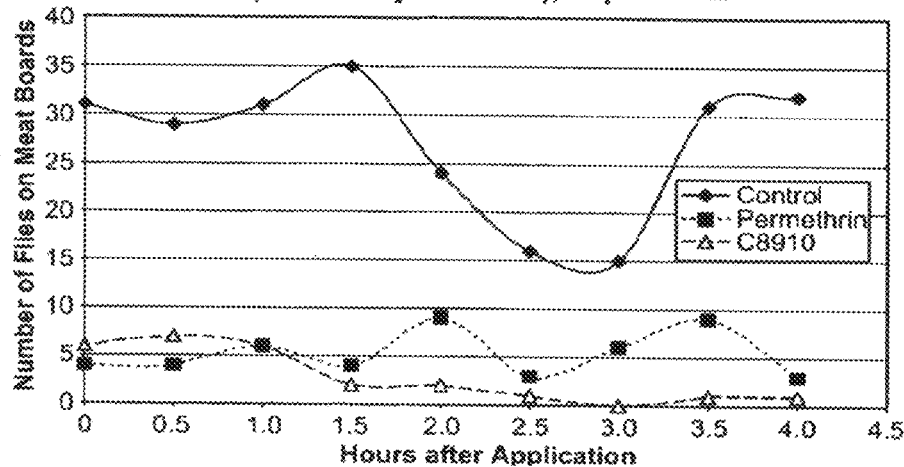
FIG. 22 shows house fly control of C8910 vs. Permethrin in Minugel 200 (Peet Grady chamber), repeat trial.
Figure 23:
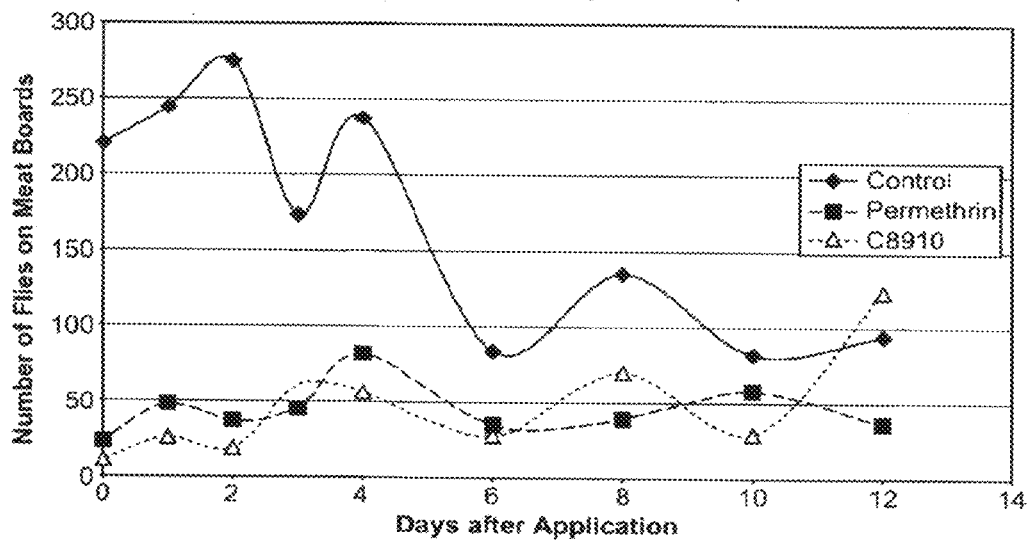
FIG. 23 shows longevity test of C8910 vs. Permethrin in LVM 40/100 for house fly control (Peet Grady chamber).

C8910 was shown to significantly reduce resting house fly or eye fly numbers in the laboratory (Peet-Grady chambers, FIGS. 20-23) or in the field (Thailand, FIG. 17-19). There were no reports of fly incapacitation from the chamber tests, as these were done with dust formulations that did not promote fly contact or absorption of C8910. There were also no reports of fly incapacitation or toxicity from the field work, as flies may have died remotely from the treatment areas.

To further investigate the incapacitating and lethal effect of the C8910 composition, water dispersions of the same formulation of C8910 were tested in the laboratory against *Aedes aegypti* mosquitoes. Graded dilutions of C8910/Kaolin-P were prepared by dispersing the powder in water (2 grams of powder in 100 ml of water, the concentration used in the field) where the lowest concentration was 0.0075% (Table 1). One ml of each dispersion was evenly pipetted over a disk of filter paper (9 cm diameter, Whatman No. 1) contained in disposable petri dishes. Approximately 15 female *Aedes aegypti* mosquitoes, 6-10 days of age, were placed in the Petri dishes and covered to prevent mosquito escape. The dishes were maintained in an environmental chamber (76-80° F. and approximately 60% humidity) and observations were made of incapacitation and mortality at various times after treatments (Table 1). At the highest dose (0.3% formulation, corresponding to the field test concentration), incapacitation was complete in 10 minutes, and mortality was 100% at 24 hours, compared to no incapacitation and 17% mortality for the lactic acid control. Lower doses of C8910 resulted in progressively less rapid incapacitation and lower mortality. While the lowest dose (0.0075% C8910 in water dispersion, 1.18 $\mu g/cm^2$) did not result in incapacitation or lethality, bioeffects were still noted in a significant reduction in spontaneous mosquito movement. Based on the low levels with which C8910 can affect mosquito behavior, the relatively low cost of actives, and the low mammalian toxicity, C8910 is useful as an area treatment for mosquito control. Similar results were obtained with house flies, stable flies, and horn flies (FIGS. 3-10).

Figure 24:
FIG. 24 shows accumulation of dead ants in the office corner where baseboards were treated with C8910 dust.
Figure 25:
FIG. 25 shows close-up of FIG. 24.

C8910 has been demonstrated to repel ants and as with flies, appears to have an incapacitative effect as well. FIGS. 24 and 25 show the corner of an office that received an application of C8910 dust around the baseboards in January of 2008. The ants continue to come indoors from a crack above the power strip, but were observed to become incapacitated, fall to the floor, and subsequently die.

Figure 26:
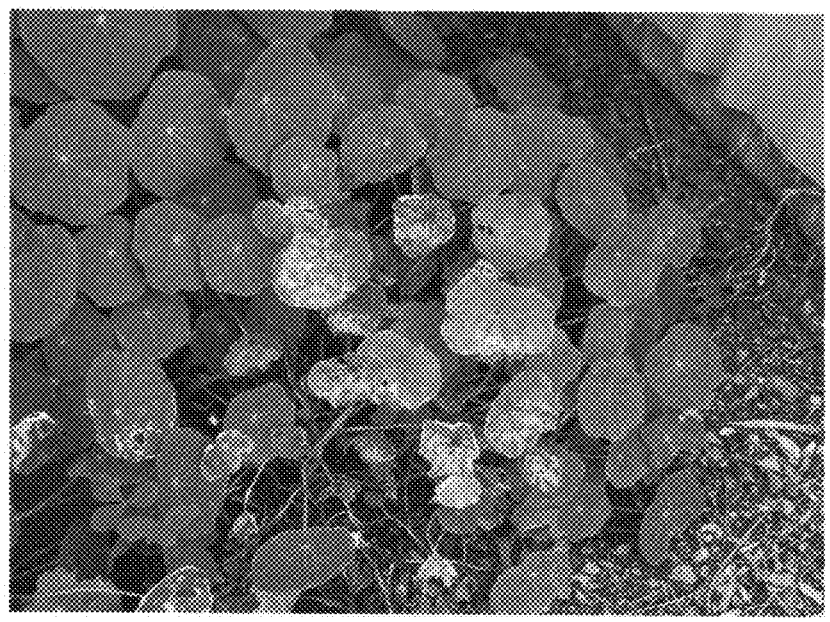
FIG. 26 shows phyto-toxicity of Evercide Emulsifiable Concentrate Vehicle. The withered treated leaves (nasturtium) in foreground are compared to control untreated leaves in background.

We have been formulating C8910 for direct application to the skin of animals, and the thrust of this effort was to minimize skin irritation and retard skin absorption, as C8910 could no longer act as a vapor repellent once it was absorbed. The best vehicles to achieve an increase in evaporation and a reduction in skin absorption are dusts and the highest measured absorption occurred with oils, with aqueous dispersions of C8910 adsorbed to clays being intermediate (Tables 2A and B, Tables 3A and B). While skin absorption of C8910 from emulsifiable concentrate (EC) vehicles was not measured, it could approach 100%, as the combination of petroleum spirits and surfactants (80:20 mix) would essentially destroy the skin barrier to penetration of xenobiotics. However, for insect control (pesticidal) applications that do not involve contact with skin or sensitive plants (FIG. 26), the goal of formulations would be to increase absorption across barrier membranes (cuticle of the insect), rather than retard absorption. Therefore, EC formulations of C8910 would serve a useful function as a treatment directed to the surface of target insects and provide a useful alternative to organophosphate or pyrethroid treatments. The aqueous dispersions of C8910 adsorbed to clay will promote absorption relative to dusts, but the absence of surfactants and petroleum distillates makes them less effective as penetration enhancers. Normally, the adsorption or organic molecules onto clay is expected to increase particle size or agglomerate the finer particles. However, the particle size of C8910/Kaolin in water was unexpectedly low (about 3 microns). This is likely due to a hydrophobic coat that the lipophilic fatty acids provided to the surface of the clay particles. The result was that this formulation is easy to aerosolize and the small particles provided increased surface area for absorption of C8910 by the insects.

IV. EXAMPLES

Example 1

Preparation of 10 kg of 15% C8910 in Emulsifiable Concentrate

Using a laboratory balance, weigh out 501.5 grams of liquid octanoic acid (99.7% purity, Cognis Corp., Cincinnati, Ohio), 543.5 grams of liquid nonanoic acid (92% purity, Cognis Corp.) and 505.0 grams of solid decanoic acid (99% purity, Cognis Corp.). The fatty acids were added together in a 4 liter beaker and magnetically stirred for approximately 2 hours so that the solid decanoic acid dissolved into the other liquid fatty acids. The emulsifiable concentrate vehicle (8450 g, Evercide without permethrin, MGK Corporation) was poured into a 5 gallon stainless steel mixing bowl and the fatty acid mixture was slowly added with stirring using a stainless steel whip attached to a Hobart mixer. After ten minutes mixing at low speed, the product was poured into a tared polyethylene storage container and the yield determined (typically 9990 grams or 99.9%).

Example 2

Preparation of 6 kg of 15% C8910 in Kaolin-P

Using a laboratory balance, weigh out 304 grams of liquid octanoic acid, 325 grams of liquid nonanoic acid and 308 grams of solid decanoic acid. The fatty acids were added together in a 2 liter beaker and magnetically stirred for approximately 2 hours so that the solid decanoic acid dissolved into the other liquid fatty acids. Pulverized kaolin clay (5003 g, Kaolin-P, U.S. Silica Corp., Kosse, Tex.) was placed into a 5 gallon stainless steel mixing bowl of a Hobart mixer. The protective screen over the mixing bowl was sealed with saran wrap to prevent any powder from escaping. The fatty acid mixture was placed in an addition funnel, whose outlet was fitted with a tygon tube to entrain the fatty acid mix through an opening in the saran wrap and into the mixing bowl. The fatty acid mix was slowly added over ten minutes with stirring using a stainless steel whip attached to a Hobart mixer. After twenty minutes mixing at low speed, any material that clung to the side of the mixing bowl was scraped off and allowed to fall into the powder. The product was then mixed for an additional five minutes. The product was removed from the mixing bowl in portions, run through a twelve inch, 30 mesh stainless steel sieve (ASTM Test Sieve, Cole Parmer, Chicago, Ill.) and collected in a tared polyethylene container to determine yield (typically 5900 grams or 98%).

Figure 27:
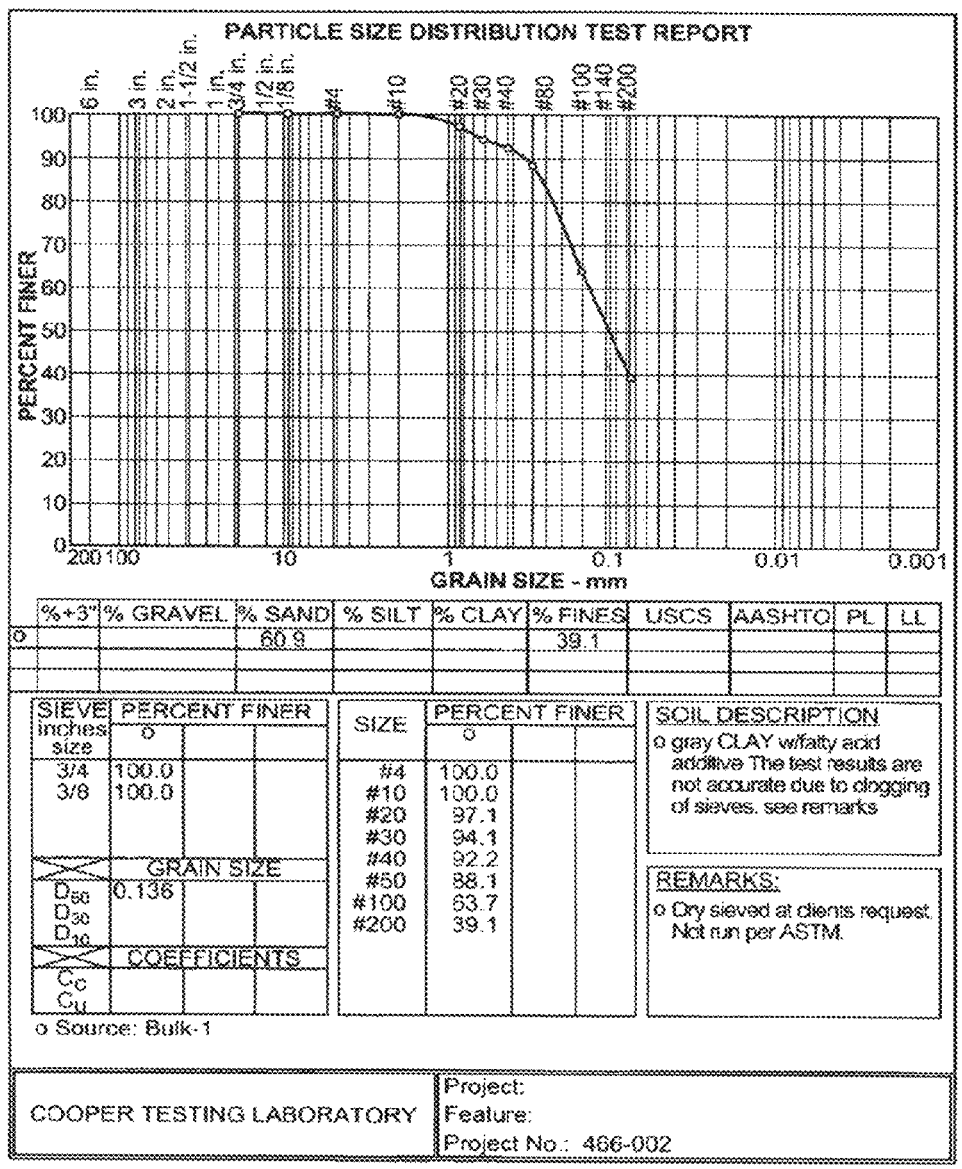
FIG. 27 shows Test Report 1. 15% C8910/Kaolin-P formulation, dry sieved, 50% finer at approximately 100 um.
Figure 28:
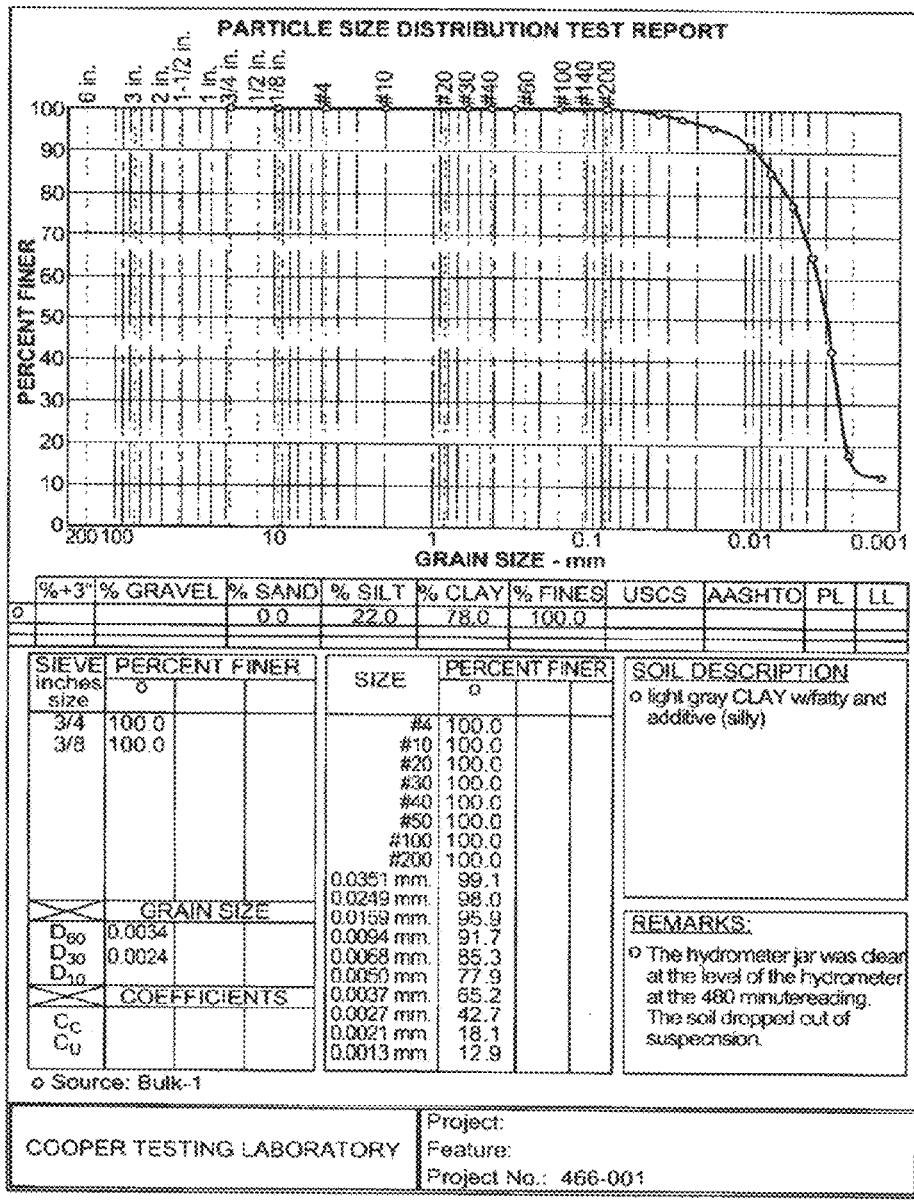
FIG. 28 shows Test Report 2. 15% C8910/Kaolin-P formulation, wet sieved, 50% finer at approximately 3 um.
Figure 29:
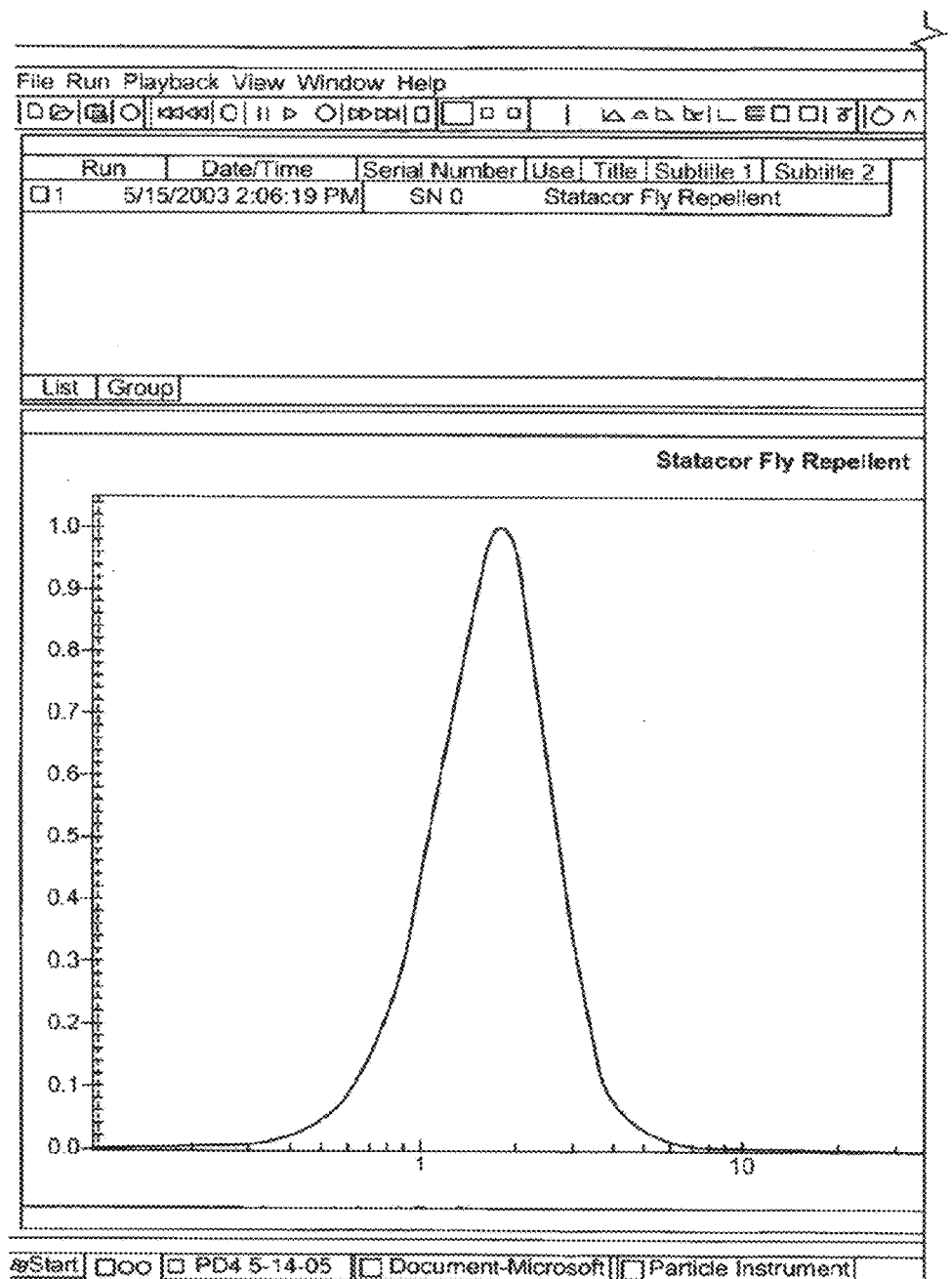
FIG. 29 shows Test Report 3, 15% C8910/Kaolin-P formulation, laser analysis, geometric mean particle size was 1.57 um.
Figure 29:
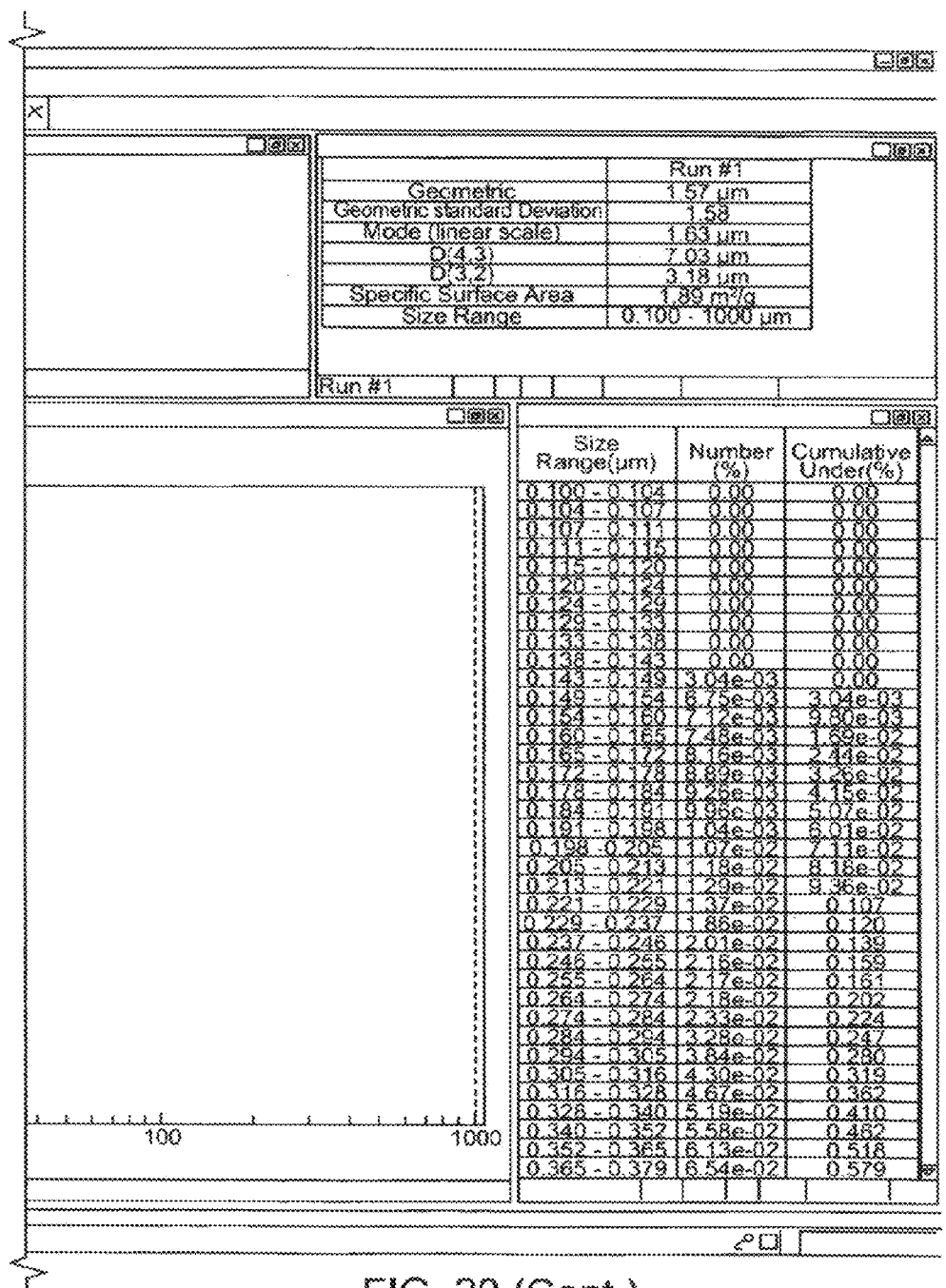

Particle size of the product was determined by dry sieving (FIG. 27), wet sieving (FIG. 28) and finally by laser analysis (FIG. 29) in which any agglomerated particles are dispersed.

The concentration of fatty acids in the kaolin clay was verified by the following analytical procedure. The fatty acids were extracted from the clay by placing an exact mass (approximately 1.0 gram) of 15% C8910/Kaolin-P in a 50 ml volumetric, followed by the addition of acetonitrile to the mark. After shaking, the fatty acids dissolved in the acetonitrile, and the clay was allowed to settle to the bottom of the volumetric. Aliquots were filtered through a 0.2 um nylon syringe filters and a 20 ul sample analyzed as follows. Analysis by HPLC was conducted with a Supelco Discovery C18 column (15 cm×4.6 mm, 5 um). The mobile phase was acetonitrile:water (50:50) with 0.1 part trifluoroacetic acid (Aldrich), at a flow rate of 1.0 ml/min using a Spectra Physics SP8800 ternary pump operated in isocratic mode. Twenty micro liter injections were done with a Spectra Physics SP8780XR auto sampler. Absorbance was monitored at 214 nm with an LDC Spectromonitor III (aufs=0.02). A pentium computer running Turbochrome software was used to process the signal from the Perkin Elmer NCI 900 interface. Under these conditions, C8 had a retention time of 5.97 minutes, C9 at 8.59 minutes, and C10 at 13.10 minutes. Certified standards of C8, C9 and C10 (Chem Sources) were used to prepare calibration plots of detector response (integration units) vs. concentration over a range of approximately 60 to 500 ug/ml. Least squares linear regression equations ($R^2$=0.99 for each of the three acids) were used to calculate fatty acid concentrations.

Example 3

Testing of C8910-Kaolin-P Clay Water Dispersions

TABLE 1

*Aedes aegypti* incapacitation and mortality as a function of C8910 dose and time after exposure to a 15% formulation of C8910 in Kaolin-P dispersed in water in amounts ranging from 0.05 grams of formulation (0.0075%) to 2 grams of formulation (0.3000%) per 100 ml water.*

| % C8910 In water dispersion | C8910 Dose, ug/cm2 | % Incapac. in 10 m exp. | % Incapac. in 25 m exp. | % Incapac. in 24 h exp. | | % motality at 24 hours | % motality at 48 hours |
|---|---|---|---|---|---|---|---|
| 0.3000 | 47 | 100 | 100 | 100 | | 100 | 100 |
| 0.0500 | 8.2 | 100 | 100 | 100 | | 67 | 100 |
| 0.0300 | 4.7 | 11 | 100 | 100 | | 12.5 | 88 |
| 0.0150 | 2.35 | 0 | 100 | 100 | | 0 | 0 |
| 0.0075 | 1.18 | 0 | 6.7 | 6.5 | (2 dead) | 6.5 | ND** |
| Lactic Acid (control) | | | | | | | |
| 0.3000 | 47(lactic acid) | 0 | 0 | 17 | (2 dead) | 17 | 17 |

*One ml of formulation was evenly dispersed on a 9 cm diameter disk of filter paper contained in a petri dish. Fifteen female *Aedes aegypti* mosquitoes were then introduced into the covered plate.

**Not determined

Notes:

1. Even at the lowest dose (1.18 ug/cm2), there are behavioral effects from C8910. Both male and female mosquitoes stop spontaneous movement, with negative consequences for mating and reproduction. This effect was not observed for the lactic acid, Kaolin-P/water or water only controls.
2. Exposure of mosquitoes to a 0.15% formulation of C8910 in Kaolin-P water dispersion for 10 minutes resulted in 100% incapacitation (2 individual plates). After 16 minutes exposure, mosquitoes were transferred to fresh plates containing only distilled water. The majority of mosquitoes remained incapacitated (83% and 100% for the two plates) 20 hours post-exposure.
3. C8910 and DEET (N,N-diethyl-m-toluamide) have similar potencies to repel *Aedes aegypti* when both are applied to the skin. The minimum effective dose (MED) of C8910 to repel mosquitoes is estimated at 25 ug/$cm^2$, the measured MED value for DEET. C8910 can incapacitate mosquitoes at doses that are ten times lower (2.35 ug/cm$^2$) and mortality at doses that are five times lower (4.7 ug/cm$^2$).

Example 4

Skin Penetration and Evaporation Studies of C8910-Kaolin-P Water Dispersions

TABLE 2A

In Vitro Cattle Skin Penetration of 3H-Octanoic Acid into Receptor Fluid as a Function of formulation

| Formulation | Physical Form | Penetration (Mean +/− S.D.) | Significance* |
|---|---|---|---|
| 15% C8910/Kaolin-P | Dust | 33 +/− 7 | A |
| 15% C8910/Kaolin-P W. Disp. | Water Dispersion | 53 +/− 5 | B |
| 15% C8910/Light Mineral Oil | Oil | 72 +/− 6 | C |

TABLE 2B

In Vitro Cattle Skin Evaporation of 3H-Octanoic Acid as a Function of Formulation

| Formulation | Physical Form | Evaporation (Mean +/− S.D.) | Significance* |
|---|---|---|---|
| 15% C8910/Kaolin-P | Dust | 41 +/− 7 | A |
| 15% C8910/Kaolin-P W. Disp. | Water Dispersion | 19 +/− 3 | B |
| 15% C8910/Light Mineral Oil | Oil | 7.0 +/− 0.7 | B |

TABLE 3A

In Vitro Cattle Skin Penetration of C-14-Decanoic Acid into Receptor Fluid as a Function of formulation

| Formulation | Physical Form | Penetration (Mean +/− S.D.) | Significance* |
|---|---|---|---|
| 15% C8910/Kaolin-P | Dust | 14 +/− 5 | A |
| 15% C8910/Kaolin-P W. Disp. | Water Dispersion | 27 +/− 11 | A |
| 15% C8910/Light Mineral Oil | Oil | 48 +/− 13 | B |

TABLE 3B

In Vitro Cattle Skin Evaporation of C-14-Decanoic Acid as a Function of Formulation

| Formulation | Physical Form | Evaporation (Mean +/− S.D.) | Significance* |
|---|---|---|---|
| 15% C8910/Kaolin-P | Dust | 22 +/− 4 | A |
| 15% C8910/Kaolin-P W. Disp. | Water Dispersion | 15 +/− 4 | A |
| 15% C8910/Light Mineral Oil | Oil | 6.0 +/− 0.5 | B |

TABLE 4A

Skin Substantivity of C8910 Formulations on Cattle Skin Based on 3H-Octanoic Acid

| Formulation | Physical Form | % Retention (Mean +/− S.D.) | Significance* |
|---|---|---|---|
| 15% C8910/Kaolin-P | Dust | 77 +/− 15 | A |
| 15% C8910/Kaolin-P W. Disp. | Water Dispersion | 87 +/− 3 | A |
| 15% C8910/Light Mineral Oil | Oil | 86 +/− 3 | A |

TABLE 4B

Skin Substantivity of C8910 Formulations on Cattle Skin Based on C-14 Decanoic Acid

| Formulation | Physical Form | % Retention (Mean +/− S.D.) | Significance* |
|---|---|---|---|
| 15% C8910/Kaolin-P | Dust | 77 +/− 18 | A |
| 15% C8910/Kaolin-P W. Disp. | Water Dispersion | 89 +/− 3 | A |
| 15% C8910/Light Mineral Oil | Oil | 88 +/− 7 | A |

*Values with the same letter designation are not significantly different

Example 5

Spray Tests with C8910/Kaolin-P Water Dispersions

A transparent canister, 7 cm in diameter and 10 cm in length, was prepared from 3 mm thick (nominal ⅛") plexiglass tubing. Fine mess cloth (cheesecloth) was secured to both ends and a 1 cm diameter hole was cut in the center of one end to allow the introduction of flies via a pipette. A cotton ball was used to block the hole once approximately 30 flies were introduced to the canister. After temporarily removing the cotton ball, test formulation or control (vehicle without actives) were sprayed into the canisters with a manual "trigger" type sprayer (Ace Hardware or equivalent) using three sprays per test. Flies were observed for incapacitation and mortality immediately after spraying, and at 24 hours post spraying.

TABLE 5

Incapacitating and Toxic Effects of C8910/Kaolin-P Water Dispersions against Flies, and Cockroaches.

| Insect | Test Material | Observation at 0.5 m | Observation at 24 h |
|---|---|---|---|
| House Fly[a] | C8910[e] | 100% incapacitation | 100% incapacitated or dead |
| House Fly | Control[f] | No effect | No effect |
| Stable Fly[b] | C8910 | 100% incapacitation | 100% dead |
| Stable Fly | Control | No effect | No effect |
| Cockroach[c] | C8910 | 100% dead | 100% dead |
| Cockroach | Control | No effect | No effect |
| Mosquito[d] | C8910 | 100% incapacitation | 100% incapacitated or dead |

[a]*Musca domestica*
[b]*Stomoxys calcitrans*
[c]German cockroach, *Blatella germanica*
[d]*Aedes aegypti*
[e]Two grams of 15% C8910 (5% each acid, octanoic, nonanoic, decanoic) in Kaolin-P (pulverized kaolin) dispersion in 100 ml of water.
[f]Two grams of Kaolin-P dispersed in 100 ml of water.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. An insect or arthropod pesticidal composition comprising:
    (a) an active ingredient comprising a mixture of fatty acids, each fatty acid having a straight carbon chain from 6 to 10 carbon atoms long, wherein the mixture of fatty acids comprises at least two of:
        (i) a first fatty acid molecule having a straight carbon chain from 6 to 8 carbon atoms long,
        (ii) a second fatty acid molecule having a straight carbon chain from 8 to 9 carbon atoms long; and
        (iii) a third fatty acid molecule having a straight carbon chain from 9 to 10 carbon atoms long, wherein the first fatty acid molecule, the second fatty acid molecule and the third fatty acid molecule are all different, wherein the amount of the composition is effective at incapacitating or killing the insect or arthropod, the mixture of fatty acids is the only active ingredient in the composition, and the active ingredient comprises at least 15% by weight of the composition; and
    (b) a carrier that promotes absorption of the active ingredient by the insect or arthropod.

2. The composition of claim 1, wherein the carrier comprises a member selected from the group consisting of an emulsifiable concentrate and a wettable powder.

3. The composition of claim 1, wherein the carrier comprises an emulsifiable concentrate.

4. The composition of claim 3, wherein the emulsifiable concentrate comprises a surfactant.

5. The composition of claim 1, wherein the carrier comprises a wettable powder.

6. The composition of claim 1, wherein the carrier comprises an organic solvent.

7. The composition of claim 1, wherein the active ingredient comprises at least 25% by weight of the composition.

8. The composition of claim 1, wherein the first fatty acid molecule comprises octanoic acid, the second fatty acid molecule comprises nonanoic acid, and the third fatty acid molecule comprises decanoic acid.

9. The composition of claim 8, wherein the first, second and third fatty acid molecules are present in about a 1:1:1 ratio by weight.

10. The composition of claim 8, wherein the first fatty acid molecule, the second fatty acid molecule and the third fatty acid molecule each comprise from about 5% to about 95% of the active ingredient.

11. The composition of claim 1, wherein
    the active ingredient comprises octanoic acid, nonanoic acid and decanoic acid at a ratio of about 1:1:1 by weight; and
    the carrier comprises a member selected from the group consisting of emulsifiable concentrate and a wettable powder.

12. The composition of claim 1, wherein the carrier comprises pulverized kaolin clay.

13. The composition of claim 12, wherein the composition has a particle site in the range of 0.5 to 4.0 microns.

14. The composition of claim 1, wherein the mixture of fatty acids comprises octanoic acid and decanoic acid.

15. The composition of claim 1, wherein the mixture of fatty acids is at least two of:
    (i) a first fatty acid molecule having a straight carbon chain from 6 to 8 carbon atoms long,
    (ii) a second fatty acid molecule having a straight carbon chain from 8 to 9 carbon atoms long; and
    (iii) a third fatty acid molecule having a straight carbon chain from 9 to 10 carbon atoms long.

16. The composition of claim 1, wherein the active ingredient does not comprise a surfactant.

17. The composition of claim 1, wherein the mixture of fatty acids comprises free fatty acids.

18. The composition of claim 1, wherein the active ingredient comprises at least 50% by weight of the composition.

19. A method for incapacitating or killing an insect or arthropod, the method comprising contacting the insect or arthropod with an effective amount of a pesticidal composition comprising:
    an active ingredient consisting of at least two of octanoic acid, nonanoic acid and decanoic acid; and
    a carrier selected from the group consisting of an emulsifiable concentrate and a wettable powder,
    thereby incapacitating or killing the insect or arthropod,
    wherein the active ingredient comprises at least 15% by weight of the composition, and wherein the active ingredient consisting of at least two of octanoic acid, nonanoic acid and decanoic acid is the only active ingredient in the method.

20. The method of claim 19, wherein the insect or arthropod is selected from the group consisting of mosquitoes, house flies, stable flies, horn flies, horse flies, face flies, eye flies, biting midges, ticks, cockroaches and ants.

21. The method of claim 19, wherein the active ingredient comprises at least 25% by weight of the composition.

22. The method of claim 19, wherein the carrier is the wettable powder.

23. The method of claim 19, wherein the carrier is the emulsifiable concentrate.

24. The method of claim 19, wherein the dose of active ingredient is about 47 μg/cm$^2$.

25. The method of claim 19, wherein the dose of active ingredient is about 25 μg/cm$^2$.

26. The method of claim 19, wherein the dose of active ingredient is about 8.2 μg/cm$^2$.

27. The method of claim 19, wherein the dose of active ingredient is about 4.7 μg/cm$^2$.

28. The method of claim 19, wherein the dose of active ingredient is about 2.35 μg/cm$^2$.

29. The method of claim 19, wherein the method selectively incapacitates or kills mosquitoes, flies, biting midges, ticks, cockroaches, and ants.

30. The method of claim 23, wherein the emulsifiable concentrate comprises a surfactant.

31. The method of claim 19, wherein the active ingredient comprises at least 50% by weight of the composition.

* * * * *